US008003847B2

(12) United States Patent
Castanedo et al.

(10) Patent No.: US 8,003,847 B2
(45) Date of Patent: Aug. 23, 2011

(54) NON-HUMAN MUTANT MAMMALS DEFICIENT IN SIGMA RECEPTORS AND THEIR APPLICATIONS

(75) Inventors: Daniel Zamanillo Castanedo, Barcelona (ES); Lluis Montoliu Jose, Barcelona (ES); Francina Langa Vives, Barcelona (ES); Alfonso Javier Lavado Judez, Barcelona (ES); Victoria Eugenia Tovar Herrador, Barcelona (ES)

(73) Assignee: Laboratorios Del Dr. Esteve, S.A., Barcelona (ES)

( * ) Notice: Subject to any disclaimer, the term of this patent is extended or adjusted under 35 U.S.C. 154(b) by 689 days.

(21) Appl. No.: 10/731,379

(22) Filed: Dec. 9, 2003

(65) Prior Publication Data
US 2005/0132429 A1     Jun. 16, 2005

(30) Foreign Application Priority Data
Dec. 9, 2002     (ES) ................... 200202815

(51) Int. Cl.
| A01K 67/027 | (2006.01) |
| A01K 67/00 | (2006.01) |
| G01N 33/00 | (2006.01) |
| C12N 15/00 | (2006.01) |
| C12P 21/06 | (2006.01) |

(52) U.S. Cl. .................... 800/8; 800/3; 800/14; 800/18; 800/21; 800/24; 800/25; 435/69.1; 435/320.1; 435/325; 435/455

(58) Field of Classification Search .................. None
See application file for complete search history.

(56) References Cited

U.S. PATENT DOCUMENTS
5,464,764 A * 11/1995 Capecchi et al. ................. 435/6

OTHER PUBLICATIONS

Seth et al., 2000, Biochemical and Biophysical Research communications 241: 535-540.*
Kaiser C., Pontecorvo M.J. & Mewshaw R.E. (1991) Sigma receptor ligands: function and activity. *Neurotransmissions* 7 (1): 1-5.
Walker J.M., Bowen W.D., Walker F.O., Matsumoto R.R., De Costa B. & Rice K.C. (1990) Sigma receptors: biology and function. *Pharmacological Reviews* 42 (4): 355-402.
Bowen W.D. (2000) Sigma receptors: recent advances and new clinical potentials. *Pharmaceutica Acta Helvetiae* 74: 211-218.
Hanner M., Moebius F.F., Flandorfer A., Knaus H.G., Striessing J., Kempner E. & Glossmann H. (1996) Purification, molecular cloning, and expression of the mammalian Sigma-i binding site. *Proceedings of the National Academy of Sciences USA* 93: 8072-8077.
Kekuda R., Prasad P.D., Fei Y.-J., Leibach F.H. & Ganapathy V. (1996) Cloning and functional expression of the human type 1 Sigma receptor (hSigmaRI). *Biochemical and Biophysical Research Communications* 229: 553-558.
Seth P., Leibach F.H. & Ganapathy V. (1997) Cloning and structural analysis of the cDNA and the gene encoding the murine type I sigma receptor. *Biochemical and Biophysical Research Communications* 241: 535-540.
Seth P., Fei Y.-J., Li H.-W., Huang W., Leibach F.-H. & Ganapathy V. (1998) Cloning and functional characterization of a receptor from rat brain. *Journal of Neurochemistry* 70: 922-931.
Prasad P.D., Hui W.L., Fei Y.-J., Ganapathy M.E., Fujita T., Plumley L.H., Yang-Feng T.-L., Leibach F.-H. & Ganapathy V. (1998) Exon-intron structure, analysis of promoter region, and chromosomal localization of the human Type 1 receptor gene. *Journal of Neurochemistry* 70: 443-451.
Crane MS (1999) Mutagenesis and cell transformation in cell culture. Methods Cell Sci. 21(4):245-253.
Earnest D.J., Liang F.Q., DiGiorgio S., Gallagher M., Harvey B., Earnest B., Seigel G. (1999) Establishment and characterization of adenoviral E1 A immortalized cell lines derived from the rat suprachiasmatic nucleus. J. Neurobiol. Apr; 39(I):1-13.
Schwartz B., Vicart P., Delouis C., Paulin D. (1991) Mammalian cell lines can be established in vitro upon expression of the SV4O large T antigen driven by a promoter sequence derived from the human vimentin gene. Biol. Cell. 73(i):7-14.
Frederiksen K., Jat P.S., Valtz N., Levy D., McKay R. (1988) Immortalization of precursor cells from the mammalian CNS. Neuron. Aug; 1(6):439-448.
Nagy A, Rossant J, Nagy R, Abramow-Newerly W, Roder JC (1993) Derivation of completely cell culture-derived mice from early-passage embryonic stem cells. *Proc Natl Acad Sci U S A* 90: 8424-8.
Kaestner KH, Montoliu L, Kern H, Thulke M & Schutz G (1994) "Universal β-galactosidase cloning vectors for promoter analysis and gene targeting". *Gene* 148: 67-70.
Kaestner KH, Hiemisch H, Schutz G. Targeted disruption of the gene encoding hepatocyte nuclear factor 3 gamma results in reduced transcription of hepatocyte-specific genes. Mol Cell Biol. Jul. 1998; 18(7):4245-51.
Capecchi MR. The new mouse genetics: altering the genome by gene targeting. Trends in Genetics Mar. 1989; 5(3):70-6.
Tybulewicz VL, Crawford CE, Jackson PK, Bronson RT, Mulligan RC. Neonatal lethality and lymphopenia in mice with a homozygous disruption of the c-abl proto-oncogene. Cell. Jun. 28, 1991; 65(7):1153-63.
DeHaven-Hudkins D.L., Fleissner LC., Ford-Rice, F.Y. (1992) Characterization of the binding of [3H]-Pentazocine to sigma recognition sites in guinea pigs brain. European Journal of Pharmacology 227:371-378.

\* cited by examiner

*Primary Examiner* — Joseph Woitach
*Assistant Examiner* — Kelaginamane T. Hiriyanna
(74) *Attorney, Agent, or Firm* — Schiff Hardin LLP

(57) ABSTRACT

The genome of the non-human mutant mammal, deficient in an endogenous Sigma receptor, contains a mutation that comprises a disruption in an endogenous Sigma receptor gene, wherein said gene disruption gives rise to a mutant lacking detectable levels of endogenous Sigma receptor. The mutant may be used as a control animal for in vivo tests, as well as a source of cells that can be used in in vitro tests. Mutants deficient in the Sigma-1 receptor can be used as models for in vivo study of disorders of the central nervous system, memory alterations, stress conditions and drug addictions, analgesia processes and neuroprotection. Mutants deficient in the Sigma-2 receptor can be used to study diagnostic or therapeutic tools to fight cancer and/or degenerative processes and/or to design compounds capable of preventing, reducing or alleviating the secondary pathology associated with administration of neuroleptic agents.

8 Claims, 14 Drawing Sheets

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial sequence
<220> FEATURE:
<223> OTHER INFORMATION: MS1 Initiator oligonucleotide

<400> SEQUENCE: 1
aattttgctc ccctcctc                                                 18

<210> SEQ ID NO 2
<211> LENGTH: 22
<212> TYPE: DNA
<213> ORGANISM: Artificial sequence
<220> FEATURE:
<223> OTHER INFORMATION: MS2 Initiator oligonucleotide

<400> SEQUENCE: 2
gcactcaaaa cttcgtcttc tc                                            22

<210> SEQ ID NO 3
<211> LENGTH: 19
<212> TYPE: DNA
<213> ORGANISM: Artificial sequence
<220> FEATURE:
<223> OTHER INFORMATION: MS3 Initiator oligonucleotide

<400> SEQUENCE: 3
cgttcacaaa tacccactg                                                19

<210> SEQ ID NO 4
<211> LENGTH: 20
<212> TYPE: DNA
<213> ORGANISM: Artificial sequence
<220> FEATURE:
<223> OTHER INFORMATION: MS4 Initiator oligonucleotide

<400> SEQUENCE: 4
```

```
agctcctctt tcccttcacc                                           20

<210> SEQ ID NO 5
<211> LENGTH: 20
<212> TYPE: DNA
<213> ORGANISM: Artificial sequence
<220> FEATURE:
<223> OTHER INFORMATION: Neo 1 Initiator oligonucleotide

<400> SEQUENCE: 5
gctattcggc tatgactggg                                           20

<210> SEQ ID NO 6
<211> LENGTH: 20
<212> TYPE: DNA
<213> ORGANISM: Artificial sequence
<220> FEATURE:
<223> OTHER INFORMATION: Neo 2 Initiator oligonucleotide

<400> SEQUENCE: 6
gaaggagata gaaggcgatg                                           20
```

NON-HUMAN MUTANT MAMMALS DEFICIENT IN SIGMA RECEPTORS AND THEIR APPLICATIONS

BACKGROUND OF THE INVENTION

The invention relates to non-human mutant mammals deficient in endogenous Sigma receptors, to the cells derived from said mutant animals, and to their application. The invention also relates to a homologous recombination vector with positive-negative selection useful for generating said non-human mutant mammals deficient in endogenous Sigma receptors.

Sigma receptors are binding sites with an affinity for different ligands, some of which are pharmaceuticals of diverse activity. Initially, the interest for Sigma receptors was due to their potential role in the actions of anti-psychotic pharmaceuticals as they showed a high affinity for typical neuroleptic agents such as haloperidol or other compounds causing psychomimetic activity, such as N-allylnormetazocine (SKF-10047). Later on it was discovered that Sigma receptors can be involved in other physiological mechanisms.

Two subclasses of Sigma receptors have been identified, known as type-1 and type-2 Sigma receptors, which can be differentiated by their pharmacological profile, function and molecular size. Both types show high to moderate affinity for typical neuroleptic agents, particularly haloperidol. However, type-1 Sigma receptors show a high affinity for (+)-pentazocine, (+)-SKF10047 and other (+)-benzo-morfanes, while type-2 Sigma receptors show a low affinity for these compounds. Type-1 Sigma receptors have a typical molecular mass of 25 kDa, while the molecular mass of type-2 Sigma receptors is 18-21 kDa (in both cases determined by photoaffinity marking).

Type 1 Sigma Receptor

The type-1 Sigma receptor, hereinafter referred to as Sigma-1 receptor, is a non-opiaceous type receptor expressed in numerous adult mammal tissues (central nervous system, ovary, testicle, placenta, adrenal gland, spleen, liver, kidney, gastrointestinal tract, etc.) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity, so that the study of the Sigma-1 receptor is of great interest in pharmacology in view of its possible physiological role in processes related to analgesia, anxiety, addiction, amnesia, depression, schizophrenia, stress, neuroprotection and psychosis. See Kaiser C., Pontecorvo M. J. & Mewshaw R. E. (1991) Sigma receptor ligands: function and activity. *Neurotransmissions* 7 (1): 1-5 (hereinafter Kaiser); Walker J. M., Bowen W. D., Walker F. O., Matsumoto R. R., De Costa B. & Rice K. C. (1990) Sigma receptors: biology and function. *Pharmacological Reviews* 42 (4): 355-402 (hereinafter Walker); and Bowen W. D. (2000) Sigma receptors: recent advances and new clinical potentials. *Pharmaceutica Acta Helvetiae* 74: 211-218 (hereinafter Bowen).

However, the actual role carried out by the Sigma-1 receptor is still unknown and enigmatic. In fact, its specific endogenous ligand is not known, although it is believed that it interacts with endogenous human steroids such as progesterone and testosterone.

The cDNA sequence encoding the Sigma-1 receptor in guinea pigs, the cDNA and Sigma-1 receptor gene in humans, the cDNA sequence and Sigma-1 receptor gene in mice and the cDNA encoding the Sigma-1 receptor in rats have all been described.

The first work to obtain a gene sequence encoding a Sigma-1 receptor is due to Hanner et al. (see Hanner M., Moebius F. F., Flandorfer A., Knaus H. G., Striessing J., Kempner E. & Glossmann H. (1996) Purification, molecular cloning, and expression of the mammalian Sigma-1 binding site. *Proceedings of the National Academy of Sciences USA* 93: 8072-8077, hereinafter Hanner).

In this work, using the specific binding characteristics of this receptor to certain radioactively marked compounds, such as (+)[$^3$H]Pentazocine, a protein first and then a cDNA clone encoding it were obtained. The clone was isolated from a cDNA genomic bank prepared from Guinea pig (*C. porcellus*) liver mRNA (cDNA with 1857 base pairs, GenBank database, access code Z66537).

Next, based on this cDNA sequence, several work groups proceeded to successively clone by sequence homology the human cDNA (see Kekuda R., Prasad P. D., Fei Y.-J., Leibach F. H. & Ganapathy V. (1996) Cloning and functional expression of the human type 1 Sigma receptor (hSigmaR1). *Biochemical and Biophysical Research Communications* 229: 553-558, hereinafter Kekuda) (cDNA with 1653 base pairs, GenBank database, access code: HSU75283), the mouse cDNA and gene (see Seth P., Leibach F. H. & Ganapathy V. (1997) Cloning and structural analysis of the cDNA and the gene encoding the murine type I sigma receptor. *Biochemical and Biophysical Research Communications* 241: 535-540, hereinafter Seth, 1997) (cDNA with 1567 base pairs, GenBank database, access code: AF030198; gene with 6973 base pairs, GenBank database, access code: AF030199), the rat cDNA (see Seth P., Fei Y.-J., Li H.-W., Huang W., Leibach F.-H. & Ganapathy V. (1998) Cloning and functional characterization of a receptor from rat brain. *Journal of Neurochemistry* 70: 922-931, hereinafter Seth, 1998) (cDNA with 1582 base pairs, GenBank database, access code: AF004218) and the human gene (see Prasad P. D., Hui W. L., Fei Y.-J., Ganapathy M. E., Fujita T., Plumley L. H., Yang-Feng T.-L., Leibach F.-H. & Ganapathy V. (1998) Exon-intron structure, analysis of promoter region, and chromosomal localization of the human Type I receptor gene. *Journal of Neurochemistry* 70: 443-451, hereinafter Prasad) (gene described in three DNA fragments respectively containing the promoter (3589 base pairs, GenBank database, access code: AF001975), the exon 1, 2 and 3 (757 base pairs, GenBank database, access code: AF001976) and the exon 4 (1630 base pairs, GenBank database, access code: AF001977)).

An analysis of the homology among these sequences, both on the basis of nucleotides and amino acids, has made manifest the high degree of homology among them. Knowledge of these sequences can be used to develop animal models intended to study the physiology and pathology associated to alterations in Sigma receptors and the effect of pharmaceuticals potentially useful for treating or preventing pathologies associated to alterations in said receptors or in which said receptors are involved.

Type-2 Sigma Receptor

The type-2 Sigma receptor, hereinafter referred to as the Sigma-2 receptor, is a receptor expressed in numerous adult mammal tissues (nervous system, immune system, endocrine system, liver, kidney, etc.). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signalling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage the DNA.

In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects. Agonists of Sigma-2 receptors can also be used in image diagnosis of cancer as agents for non-invasive visualisation of tumours and their metastasis with imaging diagnostic techniques, such as SPECT or PET. Therefore, Sigma-2 receptors constitute targets of great interest for cancer-fighting tools.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful. For more information on Sigma-2 receptors, see Bowen.

Sigma-2 receptors seem, to be involved in numerous physiological functions; however, as with Sigma-1 receptors the actual role played by Sigma-2 receptors is not entirely known, so that the need exists to increase their understanding. An alternative for contributing to the understanding of the physiological functions in which said Sigma-2 receptors are involved consists of developing animal models intended for studying the physiology and pathology in which the receptors may be involved and the effect of drugs potentially useful in the treatment and prevention of the pathologies in which said receptors are involved.

"Knockout" Technique

Genetic manipulation of mammals allows obtaining transgenic animals expressing a specific gene, or alternatively having a gene inactivated by a specific mutation ("knockout" or mutant animals). In both cases their potential use for designing experimental models in laboratory animals allowing analysing the function of a given gene in vivo is obvious.

The "knockout" technique for generating mutant animals is well established and is the object of many publications. By way of example, the following U.S. patents may be cited: U.S. Pat. Nos. 5,464,764, 5,487,992, 5,627,059, 5,631,153, 6,194,633, 6,207,876, 6,239,326, 6,245,963, 6,245,965 and 6,252,132, among others.

Lack of expression of a gene can confer a new phenotype to a mutant animal. Depending on the gene that is not expressed by the animal, it can become more or less susceptible to a given pathologic alteration. These mutant animals are valuable models for an in vivo study of the role of the gene, as well as in the study of compounds that could be potentially useful in treatment or prevention of pathologies related to the lack or expression or ineffective expression of the product of this gene.

Although Sigma receptors have been described to show an affinity for compounds with diverse pharmacological activity, the actual role played by these receptors is currently unknown, so that it is necessary to generate animal models to study in vivo the role played by endogenous Sigma receptors. A mutant animal deficient in endogenous Sigma receptors would contribute to defining the role played in vivo by these receptors and would allow designing and evaluating compounds potentially interesting for treating processes related to the null or ineffective expression of these Sigma receptors. The invention provides a solution to this current need.

SUMMARY OF THE INVENTION

The invention relates to. a non-human mutant mammal with somatic and germ cells in which at least one allele and preferably both alleles of an endogenous Sigma receptor gene contain an exogenous DNA inserted in said gene such that the mutant non-human mammal does not express the product of the endogenous Sigma receptor gene. Said Sigma receptor may be any Sigma receptor, such as Sigma-1 receptor or Sigma-2 receptor. In a specific embodiment, the exogenous DNA inserted in the endogenous Sigma gene allele comprises a positive selection marker.

Therefore, in one aspect, the invention relates to a viable non-human mammal whose genome includes the mutated Sigma receptor gene and lacks detectable levels of messenger RNA or proteins for said endogenous Sigma receptor. In a specific embodiment, said non-human mutant mammal is a non-human animal belonging to the mammal class, such as a mutant mouse deficient in the endogenous Sigma 1 receptor.

Mice deficient in the Sigma-1 receptor are viable, fertile and in laboratory conditions do not show manifest any symptoms distinguishing them from genetically similar mice lacking said mutation. In controlled stabling conditions, mice mutant in the Sigma-1 receptor are indistinguishable from their wild litter brothers. The function (or dysfunction) of the Sigma-1 receptor has been postulated to be associated to disorders in the central nervous system, such as anxiety, depression, schizophrenia or psychosis. The Sigma-1 receptor seems to have anti-amnesic and neuro-protective activity and it has been also related to perception and transduction of analgesia, addiction or stress.

For these situations, which humans may arrive at in pathologic conditions, a mouse deficient in the Sigma-1 receptor can be useful both in the study of the said situations and to validate and/or develop drugs designed to regulate or palliate the effects of the pathological alterations and conditions in which said Sigma-1 receptors are involved.

In another specific embodiment, said non-human mutant mammal is a non-human animal belonging to the mammal class, such as a mutant mouse deficient in the endogenous Sigma-2 receptor. Sigma-2 receptors seem to be targets of great interest for designing diagnostic and therapeutic tools to fight cancer and/or compounds able to prevent, reduce or alleviate the motor side effects in patients subjected to continued treatment with neuroleptic agents. Thus, mice deficient in Sigma-2 receptors could be useful for validating and/or developing drugs designed for diagnosing or treating cancer, for validation and/or developing drugs designed to prevent and/or treat degenerative processes, and to validate and/or develop drugs for preventing, reducing or alleviating the side effects associated to the continued administration to a patient of neuroleptic agents, specifically motor side effects.

The mutation in the endogenous Sigma receptor gene present in a cell genome can be inserted by homologous recombination in said cell between an allele of the endogenous Sigma receptor and a homologous recombination vector with positive-negative selection comprising regions of homology with corresponding nucleotide sequences present in said endogenous Sigma receptor gene, and selecting the recombinant homologues by the positive-negative selection technique, which are then introduced in embryos that are later implanted in receptor females for an adequate gestation that is carried to full term. The chimeras able to efficiently transmit the genotype of the recombinant homologues to their offspring via the germ line are crossed with wild non-human mammals to obtain mutant heterozygotes to disrupt the endogenous Sigma receptor gene, and later the mutant heterozygotes are crossed with one other to produce mutant homozygotes, following a classic Mendelian allele segregation.

In a specific embodiment, said non-human mutant mammal deficient in an endogenous Sigma receptor is a heterozygous mutant for said mutation, while in another specific embodiment said non-human mutant mammal is a homozygous mutant for said mutation.

The offspring of the non-human mutant mammal deficient in an endogenous Sigma receptor constitutes an additional aspect of the present invention.

In another aspect, the invention relates to cells isolated from said non-human mutant mammal deficient in an endogenous Sigma receptor, which can be propagated and optionally immortalised. These cells can be heterozygotes, i.e., containing one mutant allele and one wild type allele for the endogenous Sigma receptor gene, or homozygotes, i.e., containing two mutant alleles for the endogenous Sigma receptor gene.

In another aspect, the invention relates to a homologous recombination vector with positive-negative selection, useful for introducing a functional disruption in a Sigma receptor gene, comprising: a) a first homology region, positioned at the 5' end of a nucleotide sequence encoding a positive selection marker, wherein said first homology region has a nucleotide sequence that is substantially identical to a first sequence of a Sigma receptor gene; b) a nucleotide sequence encoding a positive selection; c) a second homology region, positioned at the 3' end of said nucleotide sequence encoding a positive selection marker, wherein said second homology region has a nucleotide sequence that is substantially identical to a second sequence of the Sigma receptor gene, the second Sigma receptor gene being positioned 3' to the aforementioned first sequence of the Sigma receptor gene in a wild type endogenous Sigma gene; and d) a nucleotide sequence encoding a negative selection marker.

In another aspect, the invention relates to a host cell in which the aforementioned homologous recombination vector with positive-negative selection has been introduced by homologous recombination between said vector and the corresponding endogenous Sigma receptor gene of said host cell, producing a functional disruption in this endogenous Sigma receptor gene. In a specific embodiment, said host cell is a differentiated cell that normally expresses the product of a Sigma receptor gene or an undifferentiated immortal pluripotent cell, such as an ES embryonic stem cell established from the internal cell mass of the embryo in the preimplantation phase known as blastocyst. In a specific embodiment, these ES embryonic cells are mouse cells.

The non-human mutant mammal of the invention can be used as an animal model for studying in vivo the role played by endogenous Sigma receptors as well as for designing and evaluating chemical compounds potentially of interest for treating pathological alterations related to the null or ineffective expression of the products of said genes, or in which said genes are involved. Additionally, said non-human mutant mammal of the invention could be used a source of cells for cell cultures.

Additional aspects of the present invention will be obvious to one in the field in view of the description and claims.

BRIEF DESCRIPTION OF THE DRAWINGS

FIG. 1A shows the pmcS1/N plasmid, corresponding to the cDNA fragment with 1020 base pairs obtained from the MS2/MS4 oligonucleotides (see Table I);

FIG. 14A is a graph representing specific binding (ordinates) of said ligand to the Sigma-1 receptors of wild homozygous, heterozygous and mutant homozygous mice as a function of ligand concentration (abscissa).

DETAILED DESCRIPTION OF THE INVENTION

Figure 1A:
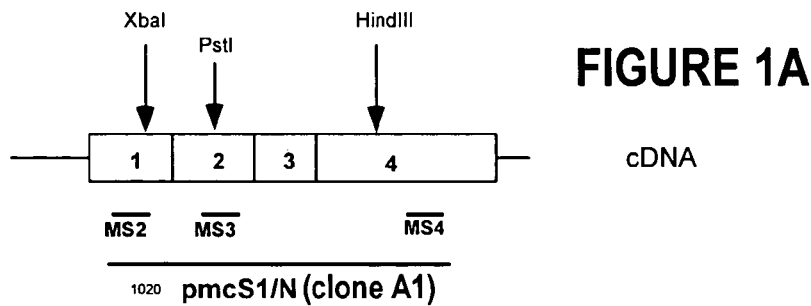
FIGS. 1A, B show schematically the first cDNA (FIG. 1A) and genomic (FIG. 1B) clones obtained by RT-PCR or PCR methods respectively.

In one of its aspects, the invention provides a non-human mutant mammal deficient in an endogenous Sigma receptor, hereinafter referred to as the non-human mutant mammal of the invention, whose genome contains a mutation comprising a disruption in an endogenous Sigma receptor gene.

The term "non-human mammal" as used in this description includes any non-human animal belonging to the mammal class, such as mice. The term "non-human mutant mammal of the invention", as used herein, refers to a non-human mammal manipulated so that it is deficient in an endogenous Sigma receptor, this is, it has a mutation preventing the normal expression of the product of a Sigma receptor gene, and thus lacks detectable levels of messenger RNA or protein for the endogenous Sigma receptor. The expression "non-human mutant mammal of the invention" includes both heterozygous mutants (those containing a mutant allele and a wild type allele of the endogenous Sigma receptor gene) and homozygotes. In a specific preferred embodiment of this invention, the non-human mutant mammal of the invention is a homozygous mutant, this is, it contains both mutant alleles of the endogenous Sigma receptor gene resulting in a non-detectable expression of the gene product.

The term "Sigma receptor", as used herein, relates to the type-1 Sigma receptor (Sigma-1) and to the type-2 Sigma receptor (Sigma-2).

The mutation present in the genome of the non-human mammal of the invention can be present in either somatic cells or germ cells of the non-human mutant mammal of the invention. Advantageously, said mutation is present in the germ cells of the non-human mutant mammal of the invention, thereby conferring to it the ability to transmit the mutation to its offspring. Therefore, in a specific embodiment of the invention, the non-human mutant mammal of the invention is fertile and can transmit its mutation to its offspring.

The mutation present in the non-human mutant mammal of the invention comprises an insertion, deletion or punctual mutation causing a functional disruption in an endogenous Sigma receptor gene, giving rise to a non-human mutant mammal deficient in said endogenous Sigma receptor. In a specific embodiment, the genome of the non-human mutant mammal of the invention comprises a transgene within the mutation inserted in the endogenous Sigma receptor gene. By way of illustration, said transgene comprises a gene encoding a positive selection marker, such as the neomycin phosphotransferase (neo) gene encoding resistance to neomycin or any other positive selection marker mentioned below in relation to the homologous recombination vector with positive-negative selection provided by this invention.

In a specific embodiment of this invention, a mutant mouse is provided deficient in the endogenous Sigma-1 receptor, homozygous for the endogenous Sigma-1 receptor gene, fertile, whose genome contains a disruption in said gene comprising the neo gene.

The non-human mutant mammal of the invention can be obtained by a process comprising the insertion of a functional disruption in an endogenous Sigma receptor gene present in a cell genome. In a specific embodiment, said functional disruption is introduced by homologous recombination in an endogenous Sigma receptor gene, such as in the Sigma-1 receptor gene or in the Sigma-2 receptor gene present in the genome of a suitable cell, such as a differentiated cell that normally expresses said Sigma receptor gene, or an ES pluripotent embryonic cell, by introducing a homologous recombination vector with positive-negative selection in said cell and selecting the recombinant homologues by the positive-negative selection technique, which can be used to generate the non-human mutant mammal of the invention as described hereinafter. Alternatively, the non-human mutant mammal of the invention can be made by classical crossing techniques, or by in vitro fertilization, between non-human mutant mammals of the invention acting as parents.

In another aspect, the invention provides recombinant clones of pluripotent embryonic ES heterozygous cells, this is, having one of the gene alleles of a Sigma receptor mutated. From these cells, it is possible to obtain chimeras and from these non-human mutant mammals deficient in a Sigma receptor. In a specific embodiment, said pluripotent embryonic ES heterozygous cells are mouse cells, from which chimeras can be obtained and, from these, mutant mice deficient in a Sigma receptor.

In another aspect, the invention provides a homologous recombination vector with positive negative selection, hereinafter the vector of the invention, comprising:

A first homology region positioned at the 5' end of a nucleotide sequence encoding a positive selection marker, wherein said first homology region has a nucleotide sequence that is substantially identical to a first sequence of a Sigma receptor gene;

A nucleotide sequence encoding a positive selection marker;

A second homology region positioned at the 3' end of said nucleotide sequence encoding a positive selection marker, wherein said second homology region has a nucleotide sequence that is substantially identical to a second nucleotide sequence of said Sigma receptor gene, this second sequence of the Sigma receptor gene being positioned at 3' to the first sequence of the Sigma receptor gene in a wild type endogenous Sigma gene; and A nucleotide sequence encoding a negative selection marker.

The Sigma receptor can be any Sigma receptor, such as a Sigma-1 or Sigma-2 receptor.

The vector of the invention can be used to insert a functional disruption in an endogenous Sigma receptor gene, such as in the Sigma-1 receptor or Sigma-2 receptor gene, contained in a cell genome by the homologous recombination technique and a positive-negative selection of the homologous recombinants, which can be used to make non-human mutant mammal deficient in an endogenous Sigma receptor.

The nucleotide sequence encoding the positive selection marker is flanked at its 5' and 3' positions by nucleotide sequences substantially identical to sequences of said Sigma receptor gene corresponding to the aforementioned first and second homology regions, respectively. As used in this description, a nucleotide sequence is "substantially identical" to a sequence of a Sigma receptor gene when said nucleotide sequence is sufficiently homologous with the sequence of said Sigma receptor gene to allow a homologous recombination between said nucleotide sequence and a sequence of the endogenous Sigma gene in a host cell. Typically, nucleotide sequences of said first and second homology regions are at least 90%, preferably 95% and more preferably 100%, identical to the nucleotide sequence of the endogenous Sigma receptor for which they are intended for homologous recombination.

Advantageously, said first and second homology regions are isogenic with respect to the endogenous allele for which they are intended (this is, the DNA of said homology regions is isolated from cells from the same gene bank as that of the cell in which the vector of the invention will be inserted). Said homology regions must be sufficiently long to allow the homologous recombination between the vector of the invention and the endogenous Sigma receptor gene in a host cell when the vector of the invention is inserted in said cell. Typically, the total length of said homology regions is at least 5 kilobases (kb), and preferably at least 10 kb.

In a specific embodiment, said first and second homology regions are chosen such that their nucleotide sequences are substantially identical to the corresponding nucleotide sequences of the endogenous Sigma receptor gene flanking a region of said gene to be eliminated by homologous recombination and replaced with the nucleotide sequence encoding a positive selection marker.

Said first and second homology regions will be chosen according to the endogenous Sigma receptor gene sequence in which a disruption will be inserted to give rise to an absence of appreciable levels of the endogenous Sigma receptor in the recombinant homologue, and thus also depending on the mutant animal deficient in the endogenous Sigma receptor to be obtained. The cDNA sequence encoding the Sigma-1 receptor in guinea pigs, the cDNA sequence and the Sigma-1 receptor gene in humans, and the cDNA sequence encoding the Sigma-1 receptor in rats have been described in Hanner, Kekuda, Seth, 1997, Seth, 1998, and Prasad.

Genomic or cDNA codes encoding endogenous Sigma-1 receptors of animals whose nucleotide sequence is still not known can be obtained by conventional methods from gene libraries for cells of such species in view of the sequences of known Sigma-1 receptor genes due to the high homology observed among them. Additionally, information on the genomic DNA or cDNA sequence pf the Sigma-2 receptor gene can be obtained from publications or databases of nucleic acid or protein sequences, or instead genomic or cDNA clones can be obtained encoding endogenous Sigma-2 receptors by conventional methods with the necessary modifications from gene libraries of cells expressing them by a strategy similar to that described in Examples 1 and 2 of this description, or by approximations similar, with the necessary modifications, to those followed by other authors to obtain the sequence encoding the Sigma-1 receptor gene (see Hanner).

Said first and second homology regions can be obtained by conventional methods, in view of the nucleotide sequence of the Sigma receptor gene in which a disruption will be introduced, such as by using a polymerase chain reaction (PCR) or RT/PCR (reverse transcription/polymerase chain reaction) using the appropriate initiator oligonucleotides. Example 1.1 describes the isolation of the mouse Sigma-1 receptor gene.

In a specific embodiment, the vector of the invention comprises a first homology region whose nucleotide sequence is substantially identical to a first nucleotide sequence of 6.8 kb of the mouse Sigma-1 receptor gene and a second homology region whose nucleotide sequence is substantially identical to a second nucleotide sequence of 3.1 kb of said gene in the mouse Sigma-1 receptor gene, delimiting a 1.9 kb sequence of said gene (see FIG. 5) that is eliminated by homologous recombination with the vector of the invention.

The nucleotide sequence encoding the positive selection marker confers a positive selection characteristic in cells containing it, that is, it allows selecting the cells containing and expressing said positive selection marker against the cells that do not contain it. The nucleotide sequence encoding the positive selection marker can be operatively bound to regulating elements that control the expression of said marker independently, constituting a positive expression cassette, or the vector of the invention can be constructed so that the expression of said marker can take place under control of the elements regulating the endogenous Sigma receptor gene.

Almost any positive selection marker can be used to construct the vector of the invention. Illustrative examples of positive selection markers can be found, for example, in the description of U.S. Pat. No. 5,464,764. In a specific embodiment, the vector of the invention contains a nucleotide sequence comprising the neo gene that confers resistance to cell mortality associated to treatment with the antibiotic neomycin or one of its analogues, such as G418 sulphate.

The nucleotide sequence encoding the negative selection marker is positioned distally, 5' or 3' to the first and second homology regions respectively, and is operatively bound to the regulating elements controlling the expression of said negative selection marker constituting a negative selection expression cassette. Advantageously, said nucleotide sequence encoding the negative marker is substantially "not identical" to any sequence of the Sigma receptor gene, so that the nucleotide sequence encoding the negative selection marker is not sufficiently homologous with any sequence of the Sigma receptor gene to allow a homologous recombination between said sequences, this is, the degree of identity between the nucleotides of said nucleotide sequence encoding the negative selection marker and the sequence of the Sigma receptor gene must be less than 45%, preferably less than 30%, in order to prevent undesired recombinations.

Furthermore, this nucleotide sequence, advantageously, is not identical to any other sequence of the non-human mammal's genome. The negative selection marker confers a negative selection marker characteristics to cells containing it, that is, it allows selecting cells that do not contain said negative selection marker from those cells containing and expressing it, as the latter will die due to the action of the negative selection agent, while those that do not contain it will survive. Although almost any negative selection marker can be used to construct the vector of the invention, the ones fulfilling the condition that the nucleotide sequence encoding said negative selection marker is not substantially identical to the nucleotide sequence of the endogenous Sigma receptor gene nor to any other sequence of the non-human mammal genome shall be selected preferably.

Examples illustrating negative selection markers can be found, for example, in U.S. Pat. No. 5,464,764. In a specific embodiment of this invention, the vector of the invention contains a nucleotide sequence comprising the thymidine kinase (tk) gene of the herpes simplex virus (HSV). The DNA synthesis can be interrupted in cells containing and expressing said tk gene. These cells can be eliminated using ganciclovir or any functionally equivalent nucleotidic analogue as a negative selection agent.

In a specific embodiment, the vector of the invention is a homologous recombination vector with positive-negative selection comprising first and second homology regions substantially identical to a first and second sequence, respectively, of the mouse Sigma-1 gene, a nucleotide sequence comprising the neo gene and a nucleotide sequence comprising the tk gene, such as the vector known as pHR53TK (see FIG. 7), deposited in the Colección Española de Cultivos Tipo (CECT) under accession number CECT 5737 on Oct. 4, 2002, which can be used to transform mouse cells, such as ES embryonic mouse cells, containing the endogenous Sigma-1 receptor gene, by homologous recombination and to obtain mouse cells, firstly with one of the mutated alleles of the endogenous Sigma-1receptor gene, and secondly, by a second homologous recombination event in the remaining wild allele of the genome, which lacks detectable levels of messenger RNA or protein for the endogenous Sigma-1receptor. Example 1.2 describes in detail the construction of the pHR53TK vector.

The homologous recombination vector with positive-negative selection provided by this invention can be constructed by conventional methods of digestion with restriction and binding enzymes and similar ones such as those described by Sambrook, Fitsch and Maniatis, eds., (1989) "Molecular Cloning: A Laboratory Manual". Cold Spring Harbor Laboratory Press, Cold Spring Harbor N.Y. (hereinafter Sambrook)

The vector of the invention allows using the "positive-negative" selection technique to select the homologous recombinants, that is, it allows selecting the cells in which this vector has been inserted as these contain and express the positive selection marker but have lost the negative selection marker as a result of the homologous recombination between the vector and the endogenous Sigma receptor gene.

The vector of the invention can be used to insert a functional disruption in an endogenous Sigma receptor gene, such as in the Sigma-1 receptor gene or the Sigma-2 receptor gene, present in the non-human mammal cell genome and create recombinant homologues (recombinant host cells) that, in turn, can be used to generate non-human mutant mammals deficient in an endogenous Sigma receptor. For this purpose, the vector of the invention is inserted in said cell by any conventional method suitable for inserting exogenous DNA in a cell, such as precipitation with calcium phosphate, transfection, microinjection, lipofection, etc., preferably by electro oration.

After introducing the vector of the invention in the host cell, the latter is cultured for a suitable period under conditions allowing the homologous recombination between the vector of the invention and the endogenous Sigma receptor gene. The homologous recombinants are selected by the positive-negative selection process and the existence of homologous recombination in the locus of the endogenous Sigma receptor gene is analyzed by conventional techniques, such as a Southern blot analysis using a probe that allows differentiating the normal endogenous allele (wild type) and the homologous recombinant allele.

Example 2.1 describes the inactivation of the mouse Sigma-1 receptor gene by homologous recombination in mouse ES embryonic cells and the production of chimerical mice (chimeras) with a mutation in the mouse Sigma-1 receptor gene by the morula aggregation technique, evaluating transmission by germ line of said mutation by crossing the respective chimeras with females of a receptor strain, such as a female of the CD-1 non-inbred strain whose albino fur is clearly distinguishable from the pigmented fur characteristic of the $F_1$ hybrid rats generated by crosses between strains 129X1/SvJ and 129S1/Sv from which the ES R1 cells used in the homologous recombination process are obtained.

The homologous recombinants (recombinant host cells) containing an allele of the mutated Sigma receptor gene can be used to make the non-human mutant mammals of the invention. For this purpose, the recombinant host cells containing a disruption in the endogenous Sigma receptor gene are introduced in embryos by conventional methods, such as by aggregating the recombinant cells with embryos in an 8-cell stage (morulae), which are then implanted in pseudogestating receptor female mammals and the embryos are allowed to come to term. The resulting animals are chimeras on which the transmittability of the mutation by germ path is analyzed. Chimeras that can efficiently transmit the genotype of the host cells to their offspring by germ line are crossed with wild type non-human mammals to obtain heterozygous mutants for disrupting the endogenous Sigma gene in somatic and germ cells. The heterozygous mutants are then crossed among themselves to obtains homozygous mutants. Example 2.2 describes the production of mutant mice (heterozygous and homozygous) for the endogenous Sigma-1 receptor gene, verifying that they were deficient in said gene as described in Example 2.3 by the corresponding structural analyzes of expression and function in homozygous mutant mice.

The offspring of a non-human mutant mammal of the invention, which constitutes an additional aspect of this invention, can be obtained by conventional methods, such as by classical crossing techniques between non-human mutant mammal of the invention (parents) or, alternatively, by in vitro fertilisation of ova and/or sperm of the non-human mutant mammal of the invention, or by cloning by nuclear transference and later reconstruction of enucleated ova with nuclei of mutant cells or embryonic or somatic cells carrying the mutation. As used in this description, the term "offspring" and "offspring of a non-human mutant mammal of the invention" relates to each and every offspring of each generation after the originally transformed non-human mammals.

The non-human mutant mammal of the invention can be used as control animals for in vivo trials (see further below). Additionally, the non-human mutant mammal of the invention can be used as a source of somatic, foetal or embryonic cells, which once isolated and cultured can be used in in vitro tests. In addition, if desired, it is possible to prepare immortalised cell lines from said cells using conventional techniques (see Crane MS (1999) Mutagenesis and cell transformation in cell culture. Methods Cell Sci. 21(4):245-253 (hereinafter Crane); Earnest D. J., Liang F. Q., DiGiorgio S., Gallagher M., Harvey B., Earnest B., Seigel G. (1999) Establishment and characterization of adenoviral E1A immortalized cell lines derived from the rat suprachiasmatic nucleus. J. Neurobiol. April; 39(1):1-13 (hereinafter Liang); Schwartz B., Vicart P., Delouis C., Paulin D. (1991) Mammalian cell lines can be established in vitro upon expression of the SV40 large T antigen driven by a promoter sequence derived from the human vimentin gene. Biol. Cell. 73(1):7-14 (hereinafter Schwartz); and Frederiksen K., Jat P. S., Valtz N., Levy D., McKay R. (1988) Immortalization of precursor cells from the mammalian CNS. Neuron. August; 1 (6):439-448 (hereinafter Frederiksen).

Thus, in another aspect, the invention provides an isolated cell line derived from the non-human mutant mammal of the invention. In a specific embodiment, the cell line provided by this invention is a murine cell line, such as a cell line of mouse ES embryonic cells comprising a mutation in the mouse Sigma-1 receptor gene in which said cell line lacks detectable levels of Sigma-1 receptor.

The non-human mutant mammals of the invention can be also used as model animals to study the role played in vivo by endogenous Sigma receptors, specifically Sigma-1 receptors or Sigma-2 receptors, and as control animals for conducting in vivo trials.

The Sigma-1 receptor seems to be involved in disorders of the central nervous system such as anxiety, depression or schizophrenia, in memory alterations, such as amnesia, and in stress and drug addiction conditions. Additionally, said Sigma-1 receptor seems to be involved in analgesia and neuroprotection processes. Thus, a non-human mutant mammal deficient in the Sigma-1 receptor, provided by this invention, can be useful in the study of such situations as well as to validate and/or develop drugs designed to regulate or alleviate the effects of the alterations and pathological conditions in which said Sigma-1 receptors are involved.

Thus, in another aspect, the invention is related to the use of a non-human mutant mammal of the invention or of a cell line provided by this invention, deficient in the Sigma-1 receptor, to evaluate potentially useful compounds meant to:
  prevent and/or treat disorders of the central nervous system, such as anxiety, schizophrenia or depression;
  prevent and/or treat memory alterations, such as amnesia;
  prevent and/or treat stress conditions;
  prevent and/or treat drug addiction conditions;
  produce analgesia; or
  produce neuroprotection.

Sigma-2 receptors seem to be targets in the design of both diagnostic and therapeutic tools for fighting cancer and/or degenerative processes and/or for designing compounds able to prevent, reduce or alleviate the secondary pathology associated with the administration of neuroleptic agents, such as motor secondary alterations caused in patients subject to continued treatment with neuroleptic agents such as haloperidol. Therefore, a non-human mammal deficient in the Sigma-2 receptor can be useful for validating and/or developing drugs designed for diagnostic and/or treatment of degenerative processes, or validating and/or developing drugs designed to prevent, reduce or alleviate the side effects associated with the continued administration to a patient of neuroleptic agents, in particular motor side effects.

Thus, another aspect of the invention relates to the use of a non-human mutant mammal of the invention, or of a cell line provided by this invention, deficient in the Sigma-2 receptor, for validating and/or developing drugs designed for:
  diagnosis or treatment of cancer;
  prevention and/or treatment of degenerative processes, or to
  prevent, reduce or alleviate the side effects associated with the administration of neuroleptic agents.

In another aspect, the invention relates to a method for determining the effect of a compound to be tested on a non-human mammal deficient in an endogenous Sigma receptor, such as a Sigma-1 receptor or a Sigma-2 receptor, that involves placing a non-human mutant mammal of the invention in contact with the compound being tested and detecting the presence or absence of a physiological change in said non-human mutant mammal as a response to the contact with said compound; or instead administering said compound to be tested to a control non-human mammal that expresses the corresponding endogenous Sigma receptor, such as the Sigma-1 receptor or the Sigma-2 receptor, and observing whether said compound has an effect on the phenotype of said non-human mutant mammal when compared with the control non-human mammal. Any observable effect on the phenotype could in principle be related to the function (or dysfunction) of the Sigma receptor considered.

In another aspect, the invention relates to a method for determining the effect of a compound on cells expressing a Sigma receptor, for example the Sigma-1 receptor or the Sigma-2 receptor, and on cells that do not express said Sigma receptor, which comprises introducing said tested compound in a cell population or in a homogenisation of said cells, wherein said cells are isolated cells or cells established from a non-human mutant mammal of the invention, administering said compound being tested to a population of control non-human mammal cells, or to a homogenisation thereof, that express the corresponding functional Sigma receptor, and observing or analyzing whether said compound being tested has an effect on the expression of said Sigma receptor in the cells of the non-human mutant mammal of the invention in comparison with the control non-human mammal cells. In principle, any observable effect on the phenotype could be related to the function (or dysfunction) or the Sigma receptor considered.

The following examples illustrate the invention and should not be considered as limiting the scope thereof. The combination of Examples 1 and 2 describes in detail a procedure for generating mice with a mutation in the endogenous Sigma-1 receptor gene that lack detectable levels of the mouse Sigma-1 receptor. Example 1 describes the isolation and cloning of the mouse Sigma-1 receptor gene and the construction of a homologous recombination vector with positive-negative selection, while Example 2 describes the transfection of ES mouse cells and the generation of mutant mice deficient in the murine Sigma-1 receptor.

EXAMPLE 1

Figure 1B:
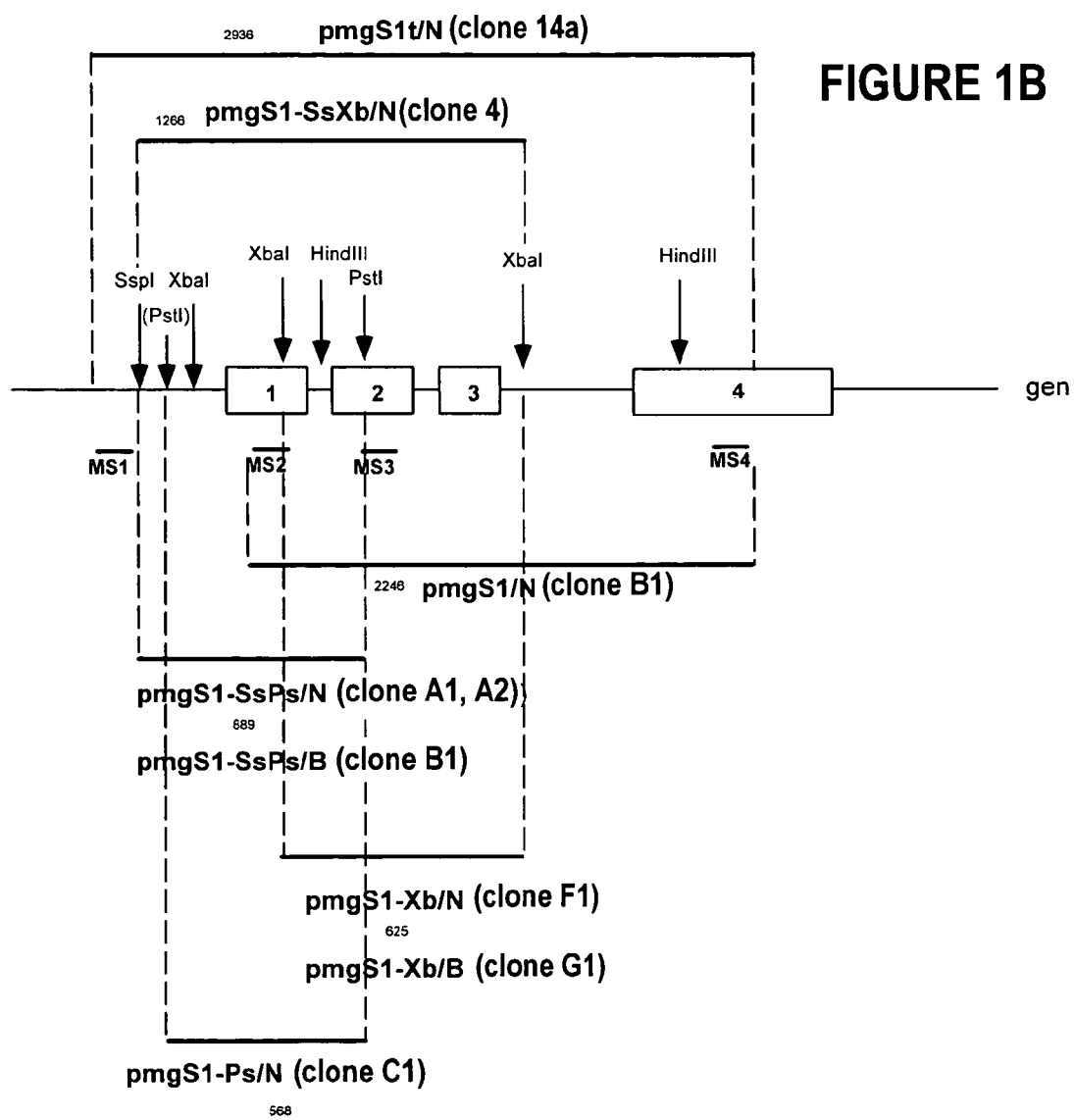

Isolation and Cloning of the Mouse Sigma-1 Receptor Gene and Construction of a Homologous Recombination Vector with Positive-Negative Selection 1.1 Isolation of the Mouse Siqma-1 Receptor Gene Using the published sequences for the mouse Sigma-1 receptor CDNA and gene (Prasad), four oligonucleotides were designed in order to isolate and clone said gene. The characteristics of these oligonucleotides, known as MS1, MS2, MS3 and MS4, are given in detail in Table I. The relative positions of these oligonucleotides with respect to the published mouse cDNA and gene sequences are schematically represented in FIG. 1.

TABLE I

Oligonucleotides used to clone the mouse Sigma-1 receptor gene

| Oligonucleotide | DNA sequence (5'->3') | Position relative to the gene [AF030199] | Position relative to the cDNA [AF030198] |
|---|---|---|---|
| MS1 | SEQ. ID. NO: 1 | 2567-2584 | — |
| MS2 | SEQ. ID. NO: 2 | 3437-3458 | 113-134 |
| MS3 | SEQ. ID. NO: 3 | 3726-3708 | 277-259 |
| MS4 | SEQ. ID. NO: 4 | 5683-5664 | 1132-1113 |

These oligonucleotides were used to obtain specific DNA fragments with the expected size from the genomic DNA and total RNA of the NMRI and BALB/C mouse strains, using standard PCR and RT/PCR protocols (Ausubel). Initially, the MS1/MS3 and MS2/MS4 oligonucleotide pairs were used, producing by PCR on genomic DNA fragments of 1160 and 2246 base pairs (bp) respectively. In addition, from total RNA by RT-PCR the cDNA corresponding to the 1020 bp fragment was cloned from the MS2/MS4 oligonucleotide pair. The DNA fragments obtained were sub-cloned in the Bluescript KS+ (Stratagene) plasmidic vector by standard methods (see Ausubel, F. M., R. Brent, R. E. Kingston, D. D. Moore, J. G. Seidman, J. A. Smith and K. Struhl. 1999. Current Protocols in Molecular Biology. John Wiley & sons, Inc., hereinafter Ausubel).

FIG. 1 describes the plasmids obtained with the cDNA and gene sequences. In particular, the pmcS1/N plasmid is described, corresponding to the 1020 bp cDNA fragment, obtained from the MS2/MS4 oligonucleotides, which was later used to obtain genomic clones of the mouse Sigma-1 receptor gene.

Cloning by PCR and RT/PCR of the various genomic and cDNA fragments corresponding to the mouse Sigma-1 receptor gene provided specific genetic probes to be used in the isolation of intact genomic clones of a mouse gene bank. As the ulterior goal is to obtain a mouse mutant in this gene, it is necessary to obtain isogenic sequence clones (i.e., from the same mouse strain) in order to optimise the homologous recombination process in the pluripotent embryonic ES cells (see A. L. Joyner (1999) "Gene Targeting. A practical approach" Second Edition. IRL Press, Oxford University Press., hereinafter Joyner).

The mouse ES cells employed, ES R1 cells (see Nagy A, Rossant J, Nagy R, Abramow-Newerly W, Roder J C (1993) Derivation of completely cell culture-derived mice from early-passage embryonic stem cells. *Proc Natl Acad Sci USA* 90: 8424-8., hereinafter Nagy), are obtained from an F1 hybrid of two 129/Sv mouse sub-strains (129X1/SvJ×129S1/SvJ). For this reason, it was decided to approach the isolation of genomic clones from a commercial gene bank prepared from DNA of 129/Sv mice (Stratagene, Cat. Nr. #946313). 1×10$^6$ recombinant clones from the gene bank were analyzed, distributed in 6 large plates (Nunc, 243 mm×243 mm, 530 cm$^2$) with 170,000 phages per plate, approximately. Two consecutive replicas were then obtained of each plate in a Nylon membrane (Hybond-N, Amersham). These membranes were hybridised with the specific probe corresponding to the pmcS1/N plasmid insert according to conventional protocols (Ausubel).

Initially, nine specific signals were identified (in both replica duplicates) and the bacteriophages present in the plates giving a positive signal were purified by conventional protocols (Ausubel). Use of the aforementioned oligonucleotides (MS1, MS2, MS3 and MS4) and a Southern blot analysis allowed verifying that four of these selected clones (λSg1, λSg2, λSg5, λSg6) contained the entire mouse Sigma-1 receptor gene.

Figure 2:
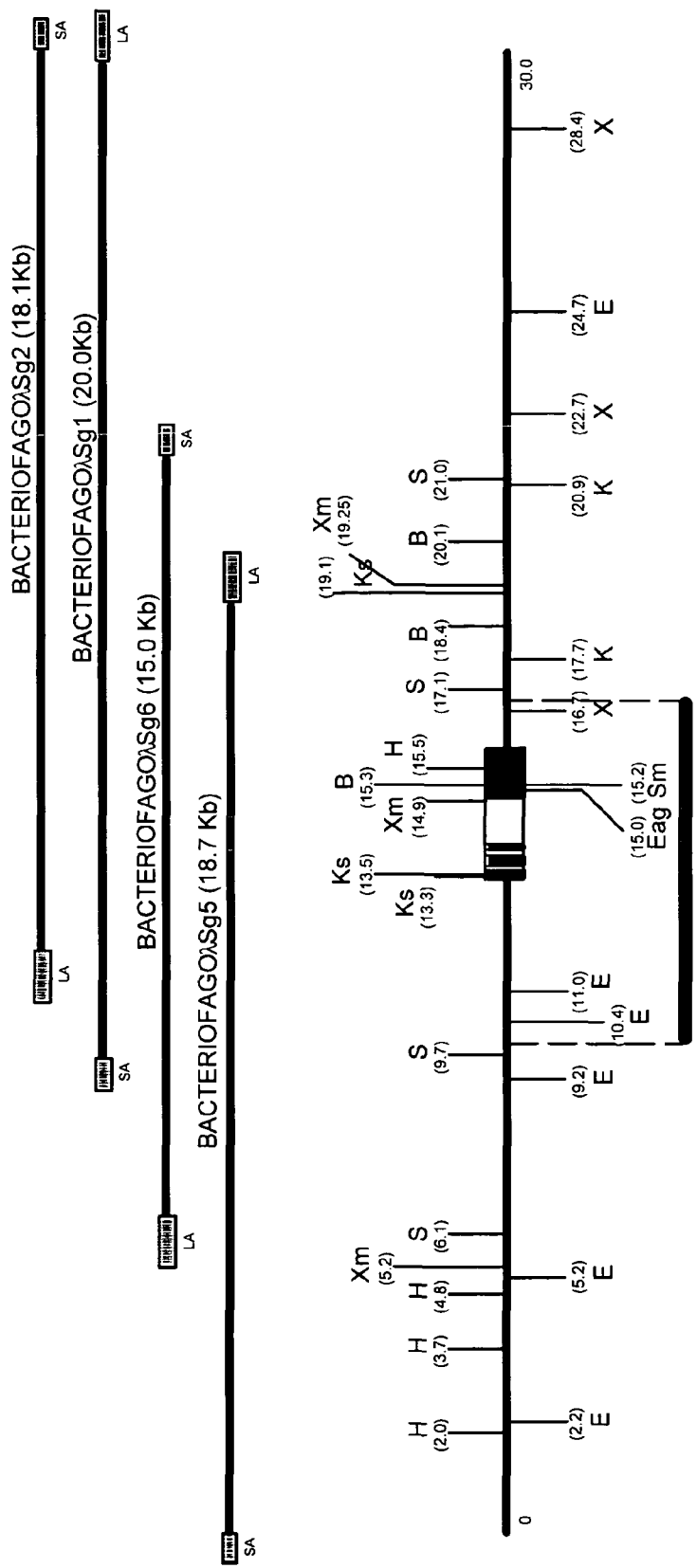
FIG. 2 shows the map of sequences adjacent to the mouse Sigma-1 receptor gene obtained by overlapping the maps corresponding to the four bacteriophage clones ($\lambda$Sg1, $\lambda$Sg2, $\lambda$Sg5, $\lambda$Sg6) isolated with the 5' and 3' sequences, surrounding the published gene sequence. The abbreviations of the restriction enzymes are described in FIG. 3. Black squares correspond to the four exons of the mouse Sigma-1 receptor gene.
Figure 3:
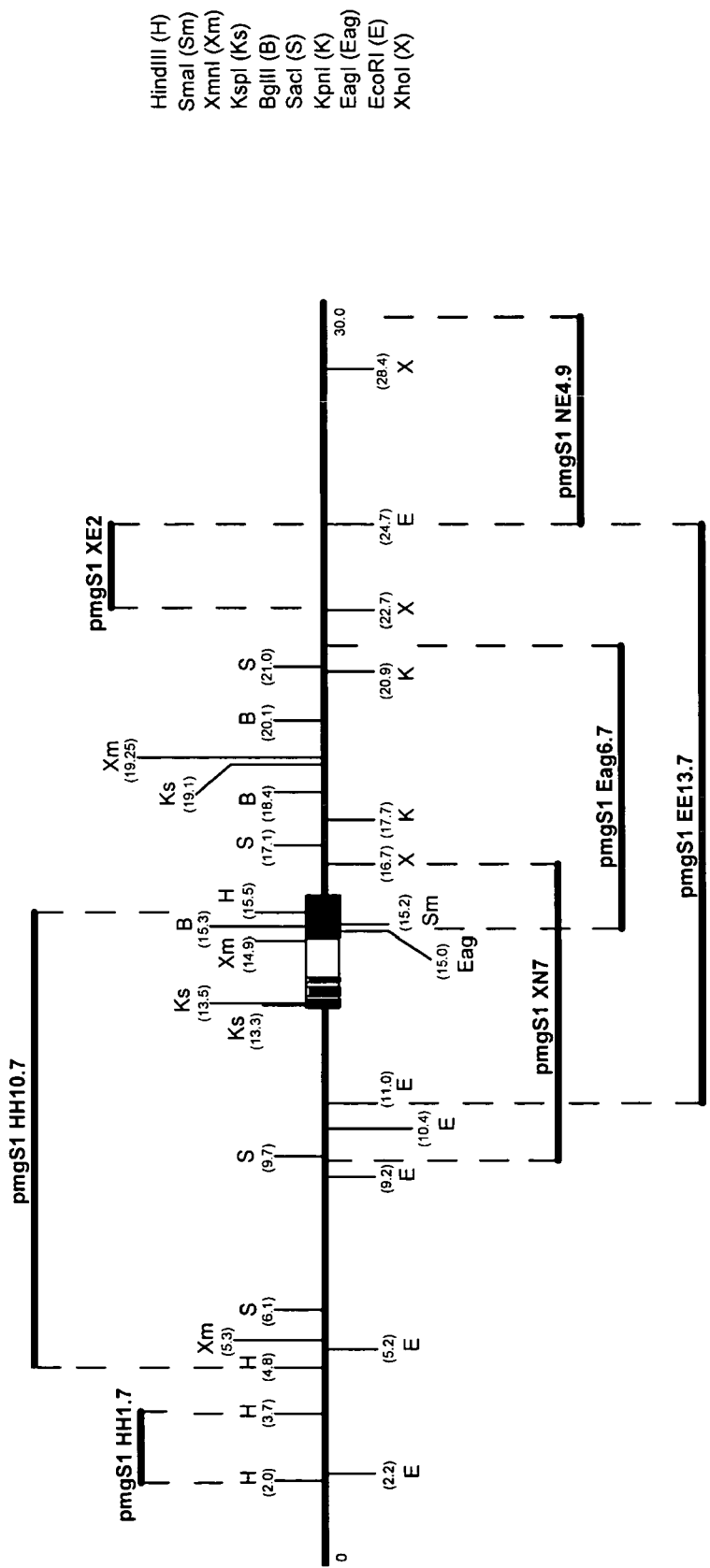
FIG. 3 shows schematically the various original plasmids obtained with genomic DNA inserts corresponding to sequences positioned at the 5' and 3' regions of the mouse Sigma-1 receptor gene, identified for subsequent use in constructing the homologous recombination vector. The restriction enzyme abbreviations are included. Black boxes correspond to the four exons of the mouse Sigma-1 receptor gene.

FIG. 2 shows the map of the sequences adjacent to the mouse Sigma-1 receptor gene obtained by overlapping the maps of the four aforementioned bacteriophage clones. The novel production was confirmed of a structural map of about 30 kilobases (kb) surrounding the gene, which exceeded published information deposited in the databases (less than 7 kb, centred around the gene) (Seth, 1997). These sequences were sub-cloned in plasmids to be used in the construction of the homologous recombination vector with positive-negative selection. FIG. 3 shows the various original clones obtained with genomic sequences corresponding to sequences positioned in the 5' and 3' gene region.

1.2 Construction of the Homologous Recombination Vector with Positive-negative Selection (pHR53TK) for Inactivation by Mutation of the Siqma-1 Receptor Gene in ES Mouse Cells In the construction of the homologous recombination vector with positive-negative selection denominated pHR53TK, the plasmid used for supporting and initiating the successive clonings was the vector pHM2 (see Kaestner K H, Montoliu L, Kern H, Thulke M & Schütz G (1994) "Universal ?-galactosidase cloning vectors for promoter analysis and gene targeting". *Gene* 148: 67-70, hereinafter Kaestner, 1994) (8451 base pairs, GenBank database, access code: X76682), which has been previously used successfully for preparing homologous recombination vectors leading to the effective inactivation of other mouse genes, see for example Kaestner K H, Hiemisch H, Schutz G. Targeted disruption of the gene encoding hepatocyte nuclear factor 3gamma results in reduced transcription of hepatocyte-specific genes. Mol Cell Biol. July 1998;18(7):4245-51, hereinafter Kaestner, 1998.

From the pmgS1 Eag6.7 plasmid (see FIG. 3), by digestion with the Bgl II restriction enzyme, a 3.1 kb fragment was obtained carrying the 3' homology sequence of the mouse Sigma-1 receptor. This 3.1 kb Bgl II fragment was inserted in the pHM2 plasmid, previously digested with the same enzyme, whose only cleavage position for Bgl II is located at the 8171 position, generating the pHR3A intermediate plasmid with a size of 11.6 kb. Next, inserted on the pHR3A plasmid, at the only cleavage site for the Pml I restriction enzyme (position 2259 relative to the pHM2 plasmid), was the 5' homology sequence of the mouse Sigma-1 receptor, obtained as a 6.8 kb fragment by digestion with the Sal I and Sac II enzymes from the DNA of the λSg6 bacteriophage (FIG. 2).

The subsequent fusion after conversion to blunt ends of the DNA sequence of the Sac II site (of the mouse Sigma-1 receptor gene sequence, position 3356 of the AF030199 sequence) and Pml I (of the pHR3A vector) allowed obtaining the functional transcription among the first four amino acids of the Sigma-1 receptor gene with the remaining amino acids of the lacZ indicator gene present in the original pHM2 vector (Kaestner, 1994). Addition of the Sigma-1 receptor gene 5' homology sequence allowed obtaining the pHR53 intermediate plasmid, which delimited precisely the nucleotides to be deleted (deletion) from the gene between the 3356 (Sac II) and 5263 (Bgl II) positions, relative to the original gene sequence deposited in GenBank AF030199. Indeed, this caused the elimination of 1907 nucleotides, which include almost all sequences encoding the mouse Sigma-1 receptor gene, with the exception of the first four amino acids.

Figure 4:
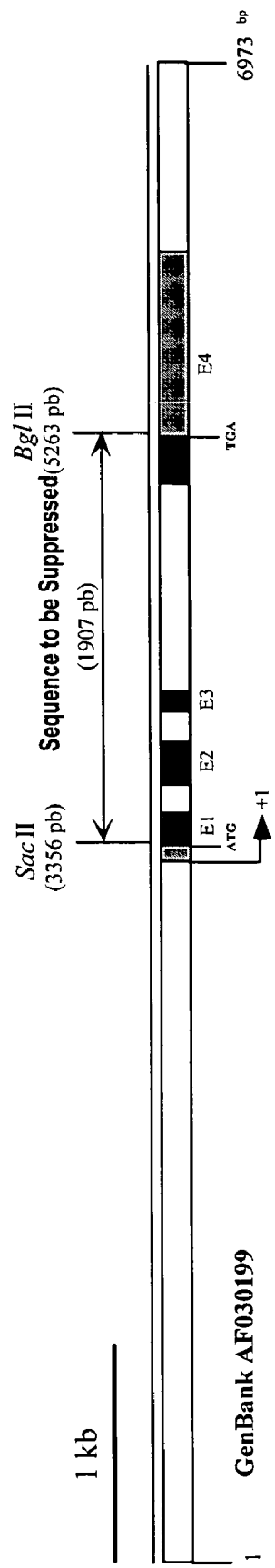
FIG. 4 shows schematically the sequence of the mouse Sigma-1 receptor gene to be eliminated by homologous recombination processes in mouse ES cells, using the AF030199 sequence as reference. Black squares represent the encoding areas, while striped squares represent the 5' and 3' sequences transcribed but not translated.
Figure 5:
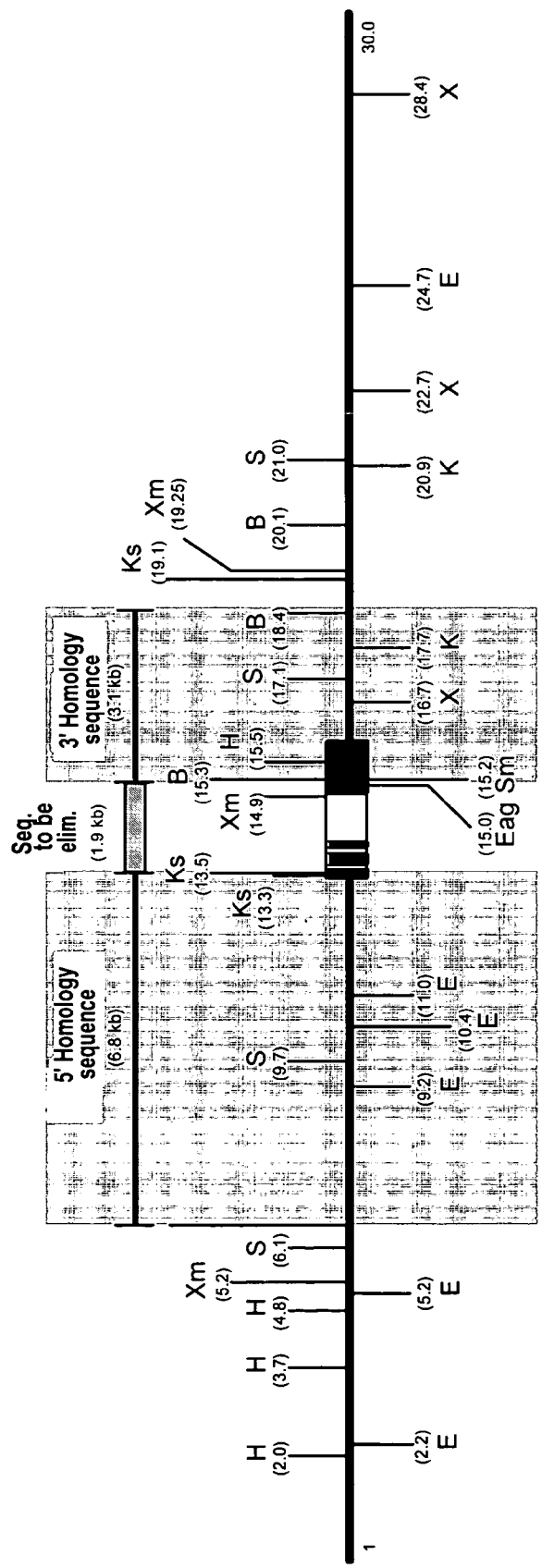
FIG. 5 shows schematically the 5' and 3' homology sequences, of 6.8 and 3.1 kb size respectively, selected for inclusion in the pHR53TK homologous recombination vector in order to inactivate the mouse Sigma-1 receptor gene. Abbreviations of the restriction enzymes are described in FIG. 3.

FIG. 4 represents graphically the accurate limits of the sequence whose elimination was intended by homologous recombination in mouse ES cells (Example 1.3). FIG. 5 shows the relative position of the 5' and 3' homology sequence positions, with size 6.8 and 3.1 present in the pHR53 vector, with respect to the aforementioned 30 kb overlapping. These 5' and 3' homology sequences in turn delimit the Sigma-1 receptor gene area to be eliminated, with a size of 1.9 kb.

Figure 6:
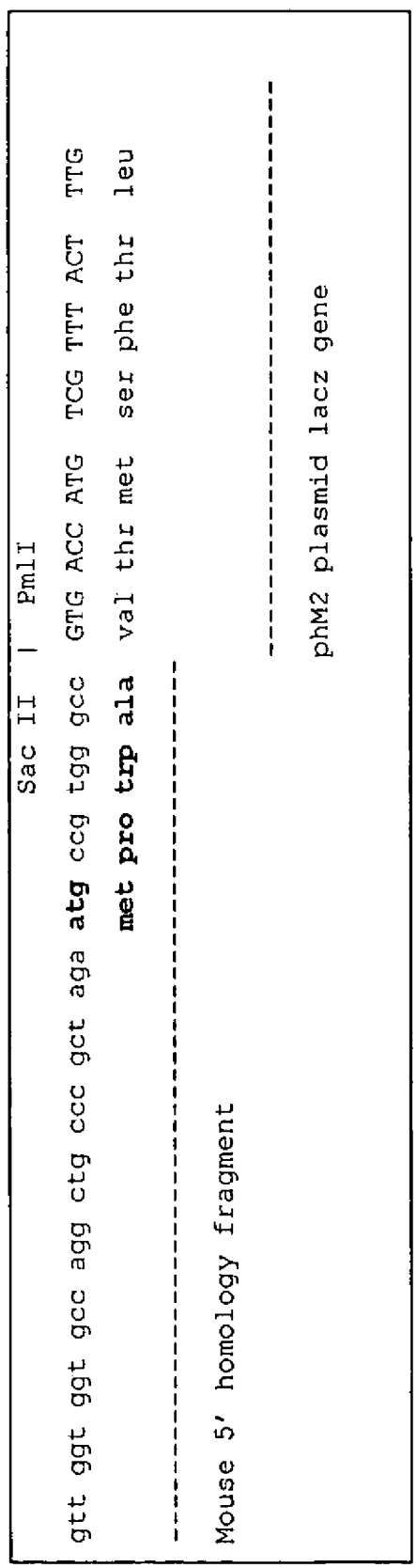
FIG. 6 illustrates the verification of the DNA sequence in the transcriptional fusion between the 5' homology region of the mouse Sigma-1 receptor gene and the first nucleotides of the lacZ indicator gene present in the pHM2 vector.

In order to verify the presence and exact fusion of the DNA fragments used to construct the pHR53 vector, their ends were sequenced. Specifically, the transcriptional fusion between the first nucleotides encoding the mouse Sigma-1 receptor gene with the sequence encoding the lacZ indicator gene was verified, as shown in FIG. 6.

Figure 7:
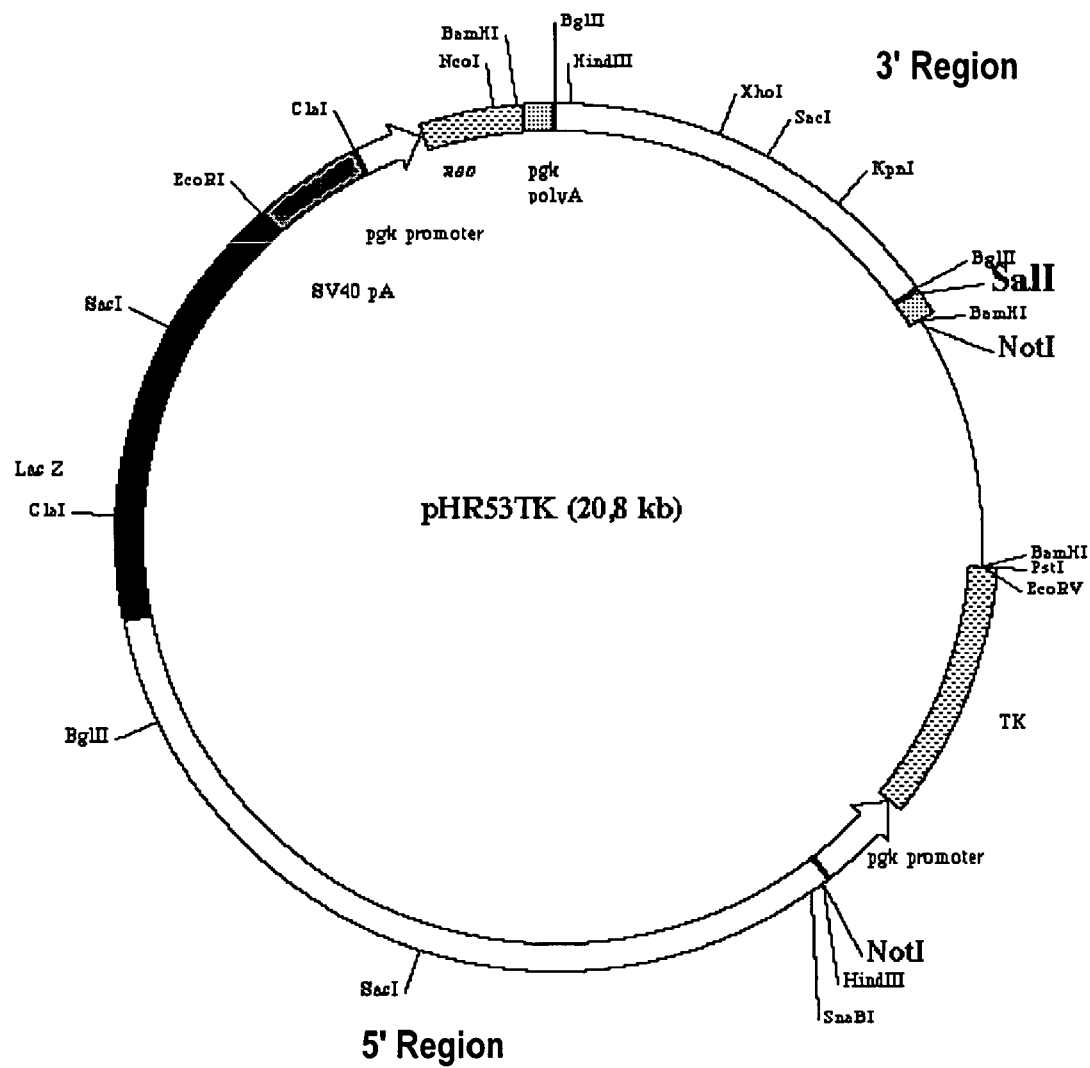
FIG. 7 shows the map of the homologous recombination vector for inactivation of the mouse Sigma-1 receptor gene in ES embryonic cells. The single restriction site Sal I is indicated, identifying the vector linearisation point for its transfection in ES cells.

Finally, in order to obtain a homologous recombination vector with positive-negative selection on which to apply the positive selection processes (neomycin resistance gene, present in the pHM2 plasmid) combined with the negative selection processes (see Capecchi M R. The new mouse genetics: altering the genome by gene targeting. Trends Genet. March 1989;5(3):70-6, hereinafter Capecchi) (ganciclovir resistance gene, herpes simplex virus thymidin kinase, HSV-TK, absent in the pHM2 plasmid but present in the pPNT (see Tybulewicz V L, Crawford C E, Jackson P K, Bronson R T, Mulligan R C. Neonatal lethality and lymphopenia in mice with a homozygous disruption of the c-abl proto-oncogene. Cell. Jun. 28, 1991;65(7):1153-63, hereinafter Tybulewicz, plasmid) the expression cassette with the HSV-TK gene was cloned in the Not I restriction site of the pHR53 plasmid by an intermediate construction in which the HSV-TK gene was obtained in the pSX (Kaestner, 1994) vector, generating on the latter plasmid the pHR53TK vector of size 20.8 kb, whose map is shown in FIG. 7. The pHR53TK plasmid has been deposited in the CECT dated 4 Oct. 2002 receiving access number CECT 5737.

The Spanish Type Culture Collection (CECT) is a service of the University of Valencia and since 1996 is an Affiliate Unit of the Agrochemistry and Food Technology Institute (IATA) of the National Research Council (CSIC). http://www.cect.org/english/index.htm

EXAMPLE 2

Generation of Mutant Mice Deficient in the Endogenous Sigma-1 Receptor Gene 2.1 Inactivation of the Sigma-1 Receptor Gene by Homologous Recombination in Mouse ES Cells and Production of Chimerical Mice with said Mutation After constructing the pHR53TK vector, it was linearised by digestion with the Sal I restriction enzyme (FIG. 7). Then 20 μg of the pHR53TK linearised vector were used to transfect $9.6 \times 10^6$ ES R1 cells (Nagy) by electroporation (electroporation conditions: 500 μF, 250 V). After 24 hours the positive selection process was initiated by adding 300 μg/ml of the G418 antibiotic. After 48 hours the drug ganciclovir was added for the negative selection process, until reaching a final concentration of 2 μM. Eight days later it was possible to identify independent recombinant clones (resistant to G418 and ganciclovir) which were sub-cultured separately. The entire process was performed in the presence of G418-resistant mouse embryonic fibroblasts (MEFs) and of L.I.F. (leukaemia inhibitory factor) growth factor in order to inhibit the spontaneous differentiation of the pluripotent ES cells. At all times protocols were followed described in the literature for culture, transfection and manipulation of mouse ES cells (Joyner) (information relative to the positive-negative selection can be found, for example, in U.S. Pat. Nos. 5,464,764, 5,487,992, 5,627,059 and 5,631,153).

Figure 8:
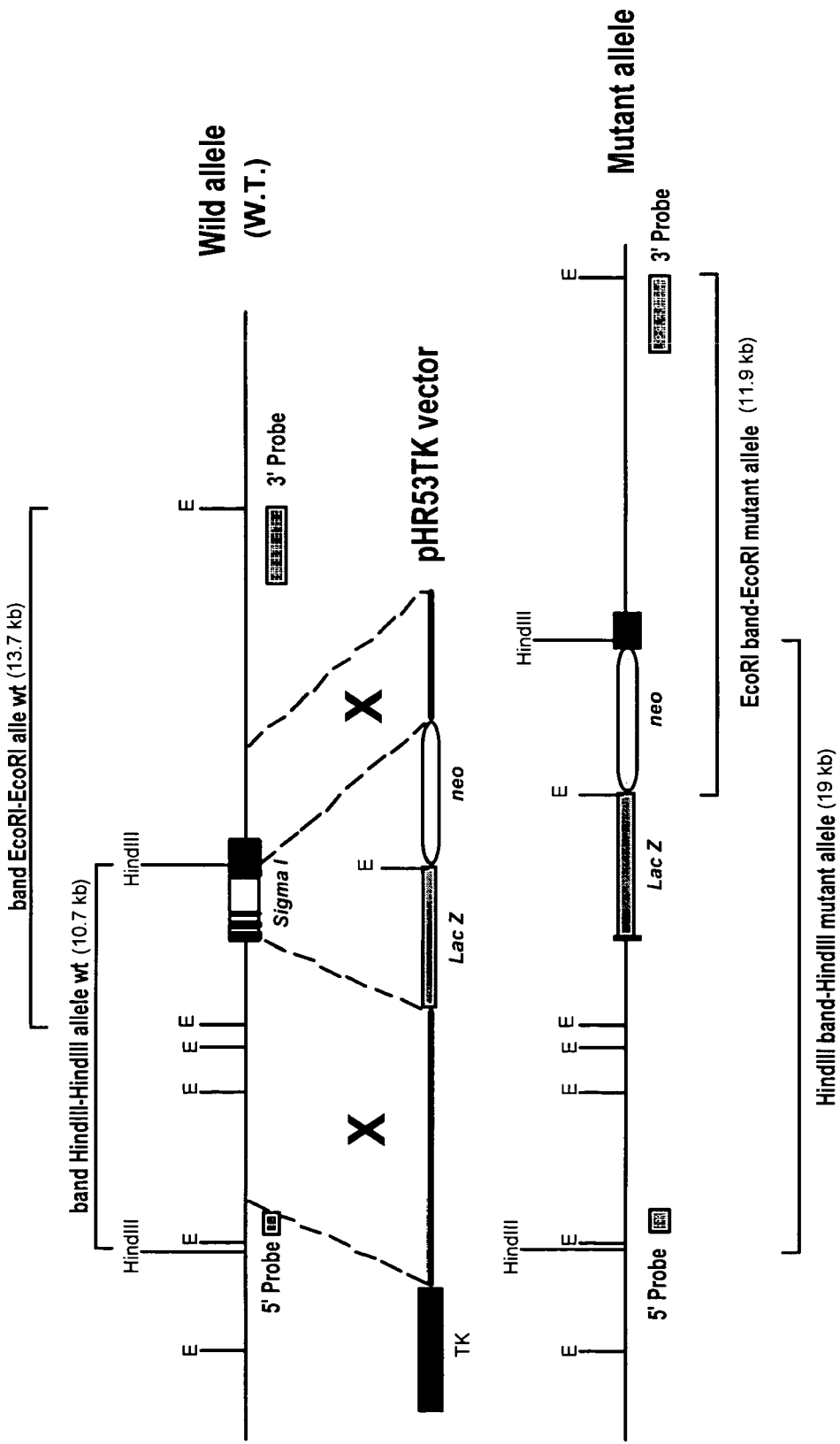
FIG. 8 illustrates the experimental design used to distinguish the mutant allele from the wild allele of the mouse Sigma-1 receptor gene in analysis by polymorphisms associated to restriction enzyme digestion in Southern blot analysis.

A total of 272 recombinant clones of mouse ES cells were analyzed by the Southern blot process, described in the Ausubel. For this purpose two probes were designed, a 5' probe and a 3' probe, distant from the homology areas of the mouse Sigma-1 receptor gene included in the pHR53TK vector in order to identify two polymorphisms in the size of restriction fragments. Thus, digestion with the Hind III restriction enzyme and use of the 5' probe allows distinguishing the wild allele (10.7 kb) from the mutant allele (19 kb) of the mouse Sigma-1 receptor gene. Similarly, digestion with the EcoR I restriction enzyme and the use of the 3' probe allows distinguishing the wild allele (13.7 kb) from the mutant allele (11.9 kb) of the mouse Sigma-1 receptor gene. FIG. 8 shows the experimental design used to differentiate the mutant and wild alleles of the mouse Sigma-1 receptor gene.

Figure 9:
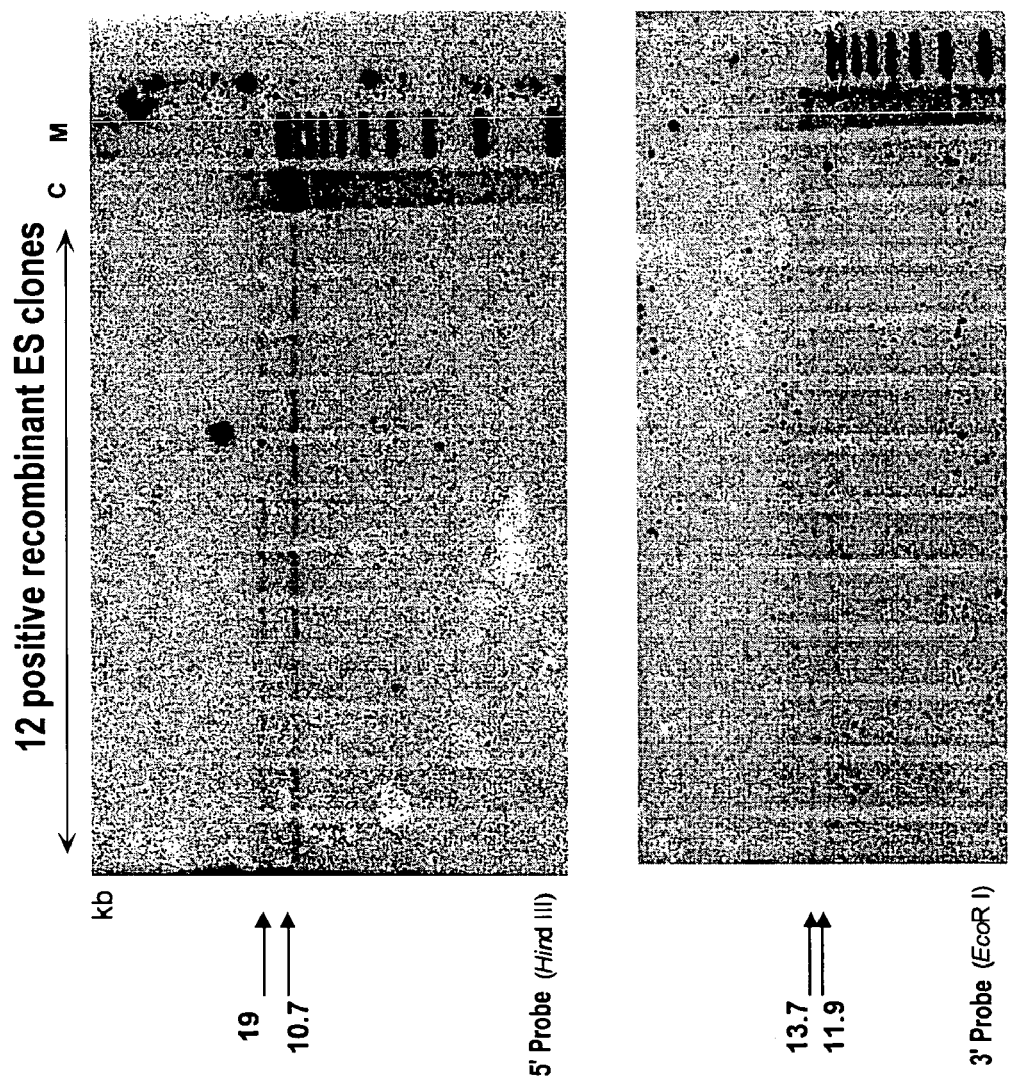
FIG. 9 shows the result of the Southern blot analysis of the genomic DNA corresponding to the 12 positive clones of the recombinant ES cell clones showing the expected polymorphisms, both with the 5' probe and the 3' probe. Lanes C and M represent control ES cell DNA and a molecular mass marker.

Of the 272 independent ES cell clones analyzed, 12 (i.e., 4.4%) showed the expected polymorphisms using the 5' probe and the 3' probe (FIG. 8). FIG. 9 shows the result of the Southern blot analyzes of the genomic DNA corresponding to these 12 ES cell clones.

Following this, 4 independent positive recombinant clones of ES cells were selected to proceed with the generation of the corresponding chimerical mice (chimeras) using the morula aggregation technique, by procedures described in Joyner and Nagy. The experimental conditions for aggregating the recombinant ES cells (in an average number of 10) with embryos in 8-cell stage (morulae) of the CD-1 mouse strain comprised the use of 4% of a conditioned medium of ES cells in the aggregation process.

Using these conditions, 11 surviving chimeras were identified obtained from 19 initially identified chimeras coming to term among the 40 fetuses that managed to advance in gestation from 382 aggregated and transferred embryos. Table II shows a summary of the aggregation process used.

TABLE II

Aggregation of morulae (8-cell mouse embryos of the CD-1 strain) with the positive recombinant ES cell clones

| No. of embryos aggregated | No. of embryos transferred (% aggregated) | No. of embryos gestated (% transferred) | No. of fetuses to term | No. of chimeras identified | No. of surviving chimeras |
|---|---|---|---|---|---|
| 399 | 382 (95.7%) | 71 (18.6%) | 40 | 19 | 11 |

The eleven surviving chimeras obtained corresponded to two clones of independent ES cells, clone #8 and clone #175, in compliance with the recommendations included in the usual protocols for chimera generation, which require obtaining the mutation from at least two independent clones to avoid problems inherent to a specific clone that could generate an anomalous phenotype of the mutant mouse (Joyner).

After this the transmission by germ line of the mutation was evaluated by crossing the corresponding chimeras with females of the CD-1 receptor strain, whose albino fur is clearly distinguishable from the pigmented fur characteristic of the 129Sv strains from which are derived the ES R1 cells used in the homologous recombination process (Nagy).

Table III describes the results of the transmission analyzes for the pigmented phenotype (associated to the genotype present in ES cells) performed on the 11 chimeras identified.

TABLE III

Chimeras obtained for mutation in the Sigma-1 receptor gene. Analysis of transmission by germ line of the genotype present in ES cells by crossing with albino CD-1 female mice

| Chimera | ES Clon | Sex | % Chimerism | % Germ Line Transmission | Pigmented F1 offspring in crosses with CD-1/ total |
|---|---|---|---|---|---|
| 1 | #175 | Male | 70% | 100% | 71/71 |
| 2 | #175 | Male | 5% | 0% | 0/130 |
| 3 | #8 | Male | 65% | 100% | 91/91 |
| 4 | #8 | Male | 20% | 0% | 0* |
| 5 | #8 | Hermaphrodite | 40% | 0% | 0** |
| 6 | #175 | Male | 50% | 0% | 0/30 |
| 7 | #175 | Male | 100% | 0% | 0* |
| 8 | #8 | Male | 70% | 100% | 27/27 |
| 9 | #8 | Male | 70% | 100% | 8/8 |
| 10 | #8 | Male | 10% | 0% | 0/28 |
| 11 | #8 | Male | 25% | 0% | 0/38 |

*Without vaginal plugs (sterile)
**Unproductive vaginal plugs (sterile)

Transmittability analyzes showed that four independent chimeras (1 derived of clone #175 and 3 derived of clone #8) were able to efficiently (100%) transmit the ES cell genotype to its offspring by gem line. These F1 animals were used to analyze the presence of the mutant allele, and by successive crossings to generate the corresponding mutant mouse.

2.2 Production of Mutant Mice in the Sigma-1 Receptor Gene

Figure 10:
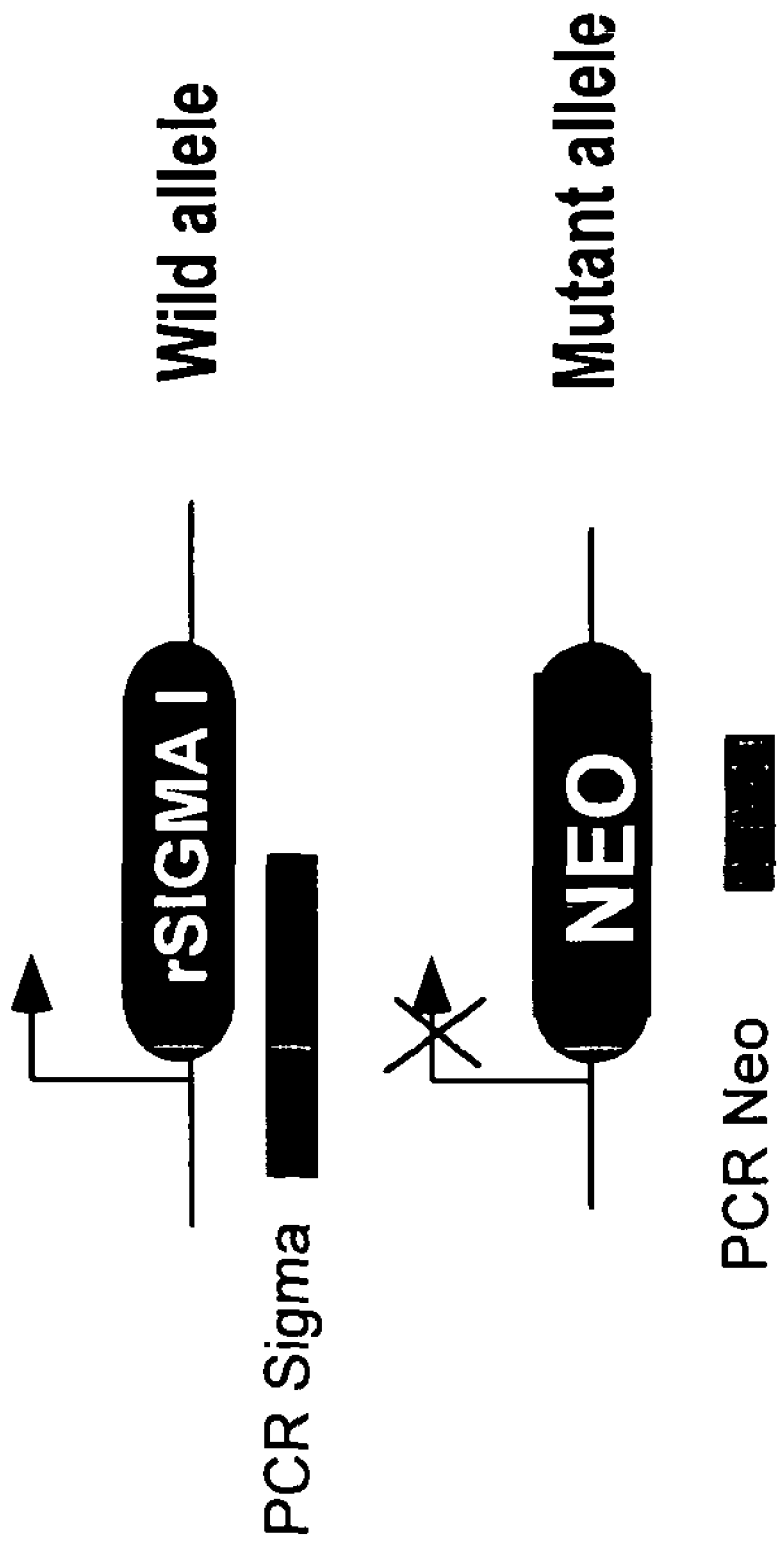
FIG. 10 shows the scheme of the PCR analytic tests used to establish the genotype of the mice carrying mutant and wild alleles of the Sigma-1 receptor gene.

After verifying the transmission to the germ line in four of the eleven chimeras obtained (with individuals representing the two recombinant ES clones used) by the presence of pigmentation in the F1 offspring obtained from crosses with CD-1 albino mice, the presence of mutated alleles of the Sigma-1 receptor gene was verified. Detecting the pigmentation does not guarantee the presence of the mutated allele as only 50% will inherit the allele carrying the mutation, while the remaining 50% will inherit the wild allele, intact, from the original ES cells. For this reason, for a later identification of the mutant and wild homozygous individuals, two analytical test were designed by the PCR technique (PCR-Sigma and PCR-Neo, FIG. 10), using conventional methods (Ausubel), that allowed an unequivocal identification of the three genotypes, specifically: wild homozygotes, heterozygotes (carrying the mutation) and mutant homozygotes (See Table IV).

TABLE IV

Obtaining the genotype by PCR

| Genotype | PCR-SIGMA | PCR-NEO |
|---|---|---|
| Wild homozygote | + | − |
| Heterozygote | + | + |
| Mutant homozygote | − | + |

The PCR-Sigma technique uses the MS1 and MS3 oligonucleotides (Table I) that can only amplify a 1.16 kb specific DNA fragment when one of the two alleles of the Sigma-1 receptor gene is intact. Similarly, PCR-Neo uses two specific oligonucleotides internal to the gene that confers resistance to neomycin (neo gene) (Neo 1 (SEQ. ID. NO: 5) and Neo 2 (SEQ. ID. NO: 6)), which amplify a 0.7 kb specific DNA fragment only if one of the two alleles carries the mutation initially detected in the ES cells.

Table V shows in detail the identification of heterozygous individuals among the individuals obtained in the F1 resulting from crossing transmitter chimeras and CD-1 females. Only pigmented individuals were analyzed by PCR-Neo. Detection of the analytical 0.7 kb band indicates that the individual carries the mutation in one of the alleles of the Sigma-1 receptor gene. Approximately half of the pigmented individuals in each of the two clones correspond to chinchilla mice. The other half are agouti mice, the wild fur colouring. Likewise, slightly under half of the pigmented F1 individuals in each of the two clones analyzed were found to be heterozygotes and thus carriers of the mutation.

TABLE V

Detection of heterozygous individuals in crosses between chimeras and CD-1 females

| Chimeras | Total number of pigmented F1 individuals analyzed by PCR | Heterozygotes (+/−) identified (% total) | Heterozygotes with chinchilla fur | Heterozygotes with agouti fur (wild) |
|---|---|---|---|---|
| Clone ES #175 | 71 | 31 (43.7%) | 14 | 17 |
| Clone ES #8 | 112 | 51 (45.5%) | 25 | 26 |

After enough heterozygous individuals were identified (of both sexes) of each ES clone used, crosses were made between these heterozygous individuals in order to obtain, according with Classical Genetics (Mendelian) laws, mutant individuals (homozygous for the mutant allele) in the second generation (F2) obtained.

The genotypes obtained for the F2 animals generated were based on the two aforementioned PCR analytical tests (PCR-Sigma and PCR-Neo) (see Table IV). The result of these crosses and the total numbers of each of he three genotypes obtained for the second-generation individuals are given in Table VI.

TABLE VI

Detection of homozygous individuals in crosses between F1 animals

| Clones | Total F2 individuals analyzed by PCR | Wild individuals (+/+) identified | Heterozygous individuals (+/−) identified | Mutant homozygous individuals (−/−) identified |
|---|---|---|---|---|
| Clone ES #175 | 130 | 42 | 60 | 28 |
| Clone ES #8 | 48 | 12 | 25 | 11 |

According to Mendel's laws, the result of crossing two heterozygous individuals with two different alleles for the same locus will be distributed as follows: 25% wild individuals (+/+), 50% heterozygous individuals (+/−) and 25% mutant homozygous individuals (−/−). Table VII compares the results obtained in F2 (Table VI) without those expected according to Mendel's laws.

TABLE VII

Comparison between expected results and obtained results for F2 individuals

| | Total F2 individuals | Wild (+/+) (% total) | Heterozygotes (+/−) (% total) | Mutant (−/−) (% total) |
|---|---|---|---|---|
| Clone ES #175 Results OBTAINED | 130 | 42 (32.3%) | 60 (46.2%) | 28 (21.5%) |
| Clone ES #175 Results EXPECTED | 130 | 32.5 (25%) | 65 (50%) | 32.5 (25%) |
| Clone ES #8 Results OBTAINED | 48 | 12 (25%) | 25 (52.1%) | 11 (22.9%) |
| Clone ES #8 Results EXPECTED | 48 | 12 (25%) | 24 (50%) | 12 (25%) |

The statistical analysis of these data leads in both cases to a calculated $\chi^2$ value lower than that tabulated for p=0.05 and (3−1=2) 2 degrees of freedom ($\chi^2$=5.991) (Clone ES #175 $\chi^2$=3.785; Clone ES #8 $\chi^2$=0.125) so that it is possible to conclude that the genotype distribution fits that predicted by Mendel (p=0.05). Thus, slight reduction in mutants identified with respect to the theoretically expected values is not statistically significant.

As an additional conclusion to this first analysis, it should be added that mutant homozygous males and females are equally obtained. The sex distribution of the mutant homozygotes identified fits the expected values (50% of each sex), not observing any statistically significant deviations at this point. In the case of clone ES #175, of the 28 mutants detected 13 are male, which in the case of clone ES #8 of the 11 mutants detected 4 are male. Both values approach normality and follow the expected distribution (p=0.05, degrees of freedom=1, $\chi^2$ calculated=3,841) (Clone ES #175 $\chi^2$=0.143; Clone ES #8 $\chi^2$=0.818).

Additionally, it has been found that both male and female mutant homozygotes are fertile, so that it has been possible to obtain stable colonies of this mutation. No external or observable manifestations have been found that apparently differentiates mutant mice from wild mice. However, the mice are being thoroughly analyzed to evaluate the effect of the mutation in the Sigma-1 receptor gene by paradigms meant to elucidate its role in processes of analgesia, addiction, depression, psychosis and schizophrenia using conventional methods in this field (see Jacqueline N. Crawley (2000) What's wrong with my mouse?. *Behavioral phenotyping of transgenic and knockout mice*, Wiley-Liss, New York, hereinafter Crawley).

The mutation has been obtained and analyzed in two different mixed gene banks (129Sv×CD-1 and 129Sv×C57BL/6J).

2.3 Structural, Expression and Function Analyzes in Mutant Mice for the Siqma-1 Receptor Gene After the mouse Sigma-1 receptor gene mutant mice were generated, the absence of the gene (DNA), its expression (messenger RNA), the protein and activity (function) were analyzed to verify that, indeed, the mutant mice were deficient in the Sigma-1 receptor gene.

Figure 11:
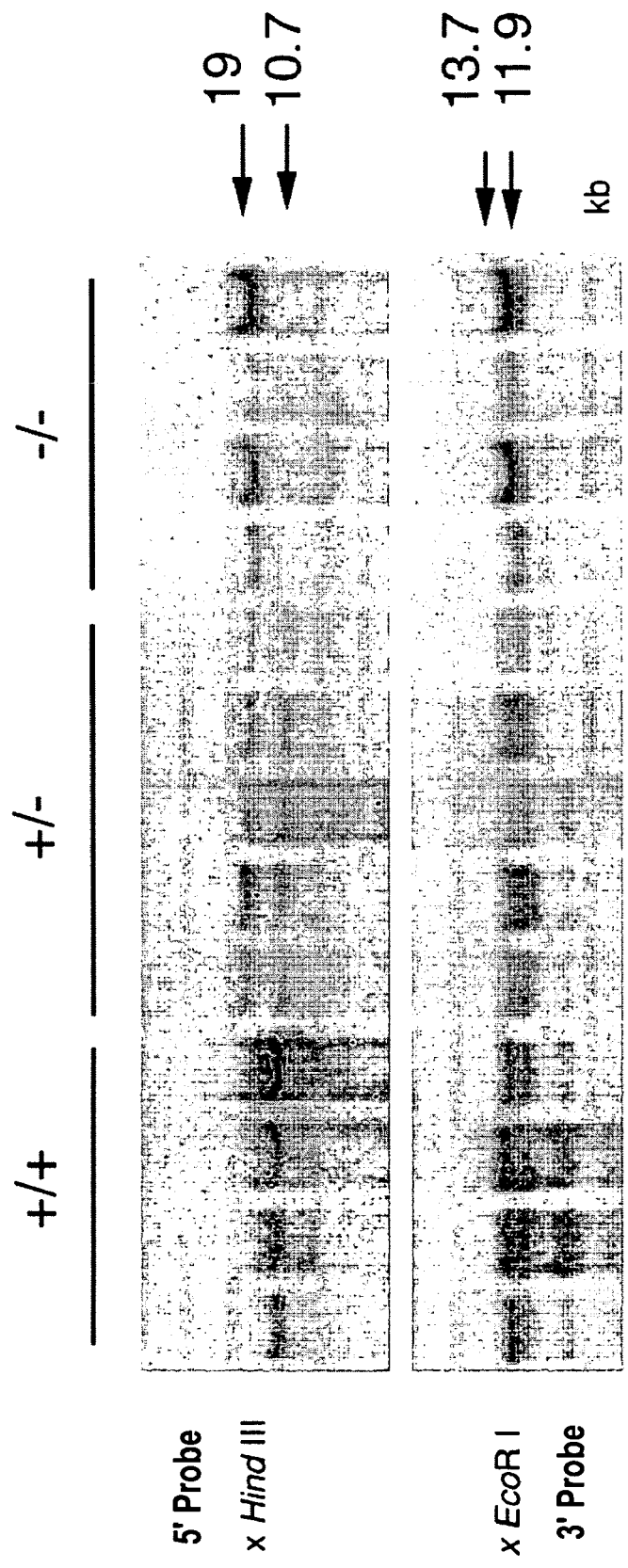
FIG. 11 shows the results of the Southern blot analyzes of wild homozygotes (+/+), heterozygotes (+/−) and mutant homozygotes (−/−) by digestion of genomic DNA with the Hind III and EcoR I enzymes and consecutive hybridisation with the 5' and 3' probes, respectively. The size of the DNA fragments correspond to the values expected by the experimental design (FIG. 8)

Firstly studied was the presence of polymorphisms associated to probes 5' and 3', which allow detecting the mutant and wild alleles unequivocally. For this, genomic DNA of wild, heterozygous and mutant mice in the Sigma-1 receptor gene was analyzed. The result of the Southern blot analysis is shown in FIG. 11. The results obtained allow unequivocally concluding the presence of the mutant allele according to the expected experimental design.

Figure 12:
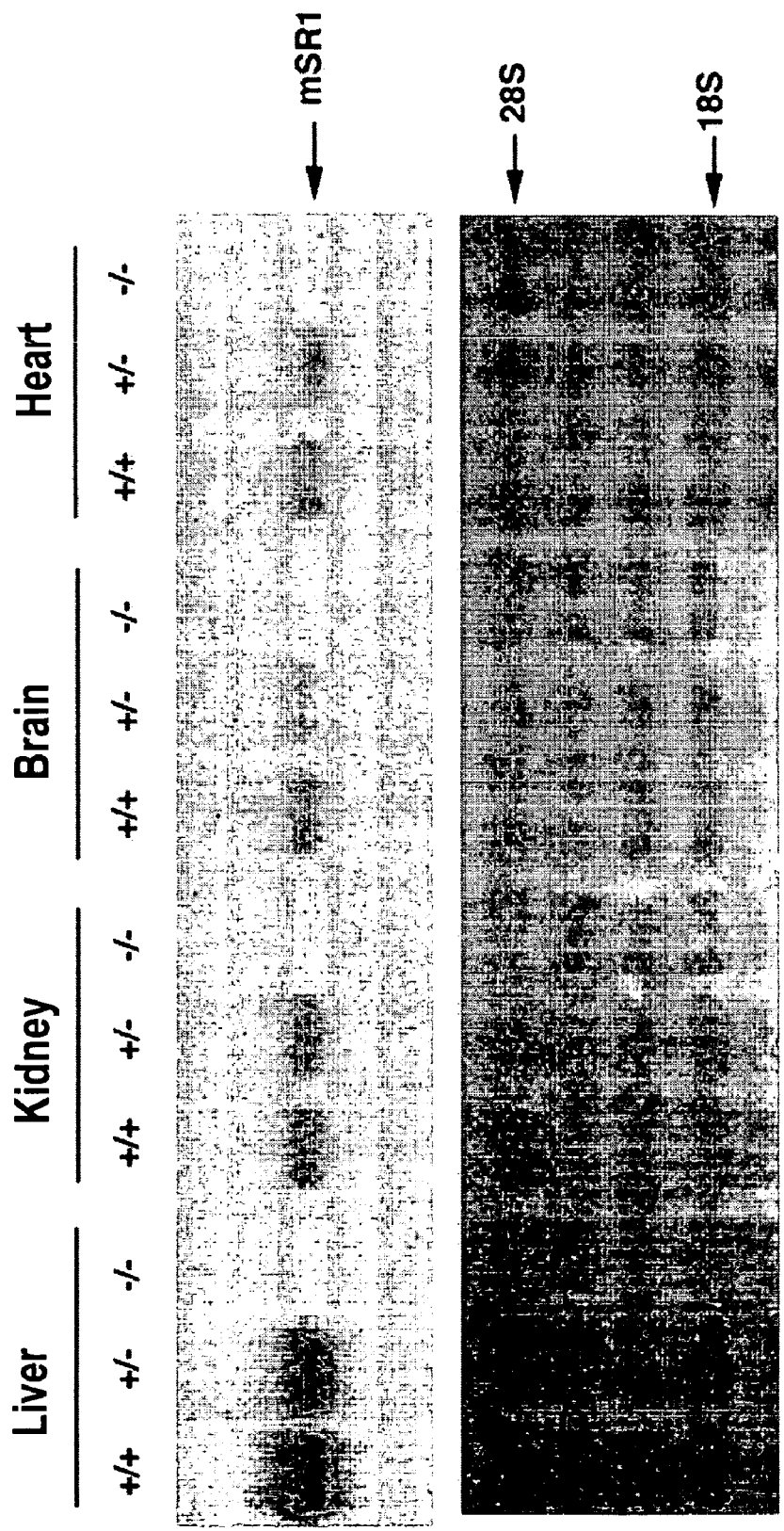
FIG. 12 shows the results of the Northern blot analyzes of the mouse Sigma-1 receptor (mSR1) in total liver, kidney, brain and heart isolated RNA from mouse wild homozygotes (+/+), heterozygotes (+/−) and mutant homozygotes (−/−). The photograph of the ribosome RNA used as load control is included in the bottom area.

Secondly, the expression of the Sigma-1 receptor gene in various organs of mutant, heterozygous and wild mice in which the gene is normally present was studied (Kekuda). These expression analyzes were performed by the Northern blot technique, following the protocols described in the field (Ausubel). FIG. 12 below shows the absence of signal in the gel lanes corresponding to the total RNA of mutant homozygous animals, which therefore lack the Sigma-1 receptor gene. Therefore, not only is the Sigma-1 receptor gene missing but it is also impossible to find messenger RNA (transcriptions) allowing it to document its expression. Indeed, the mutant mouse does not express the Sigma-1 receptor gene.

Figure 13:
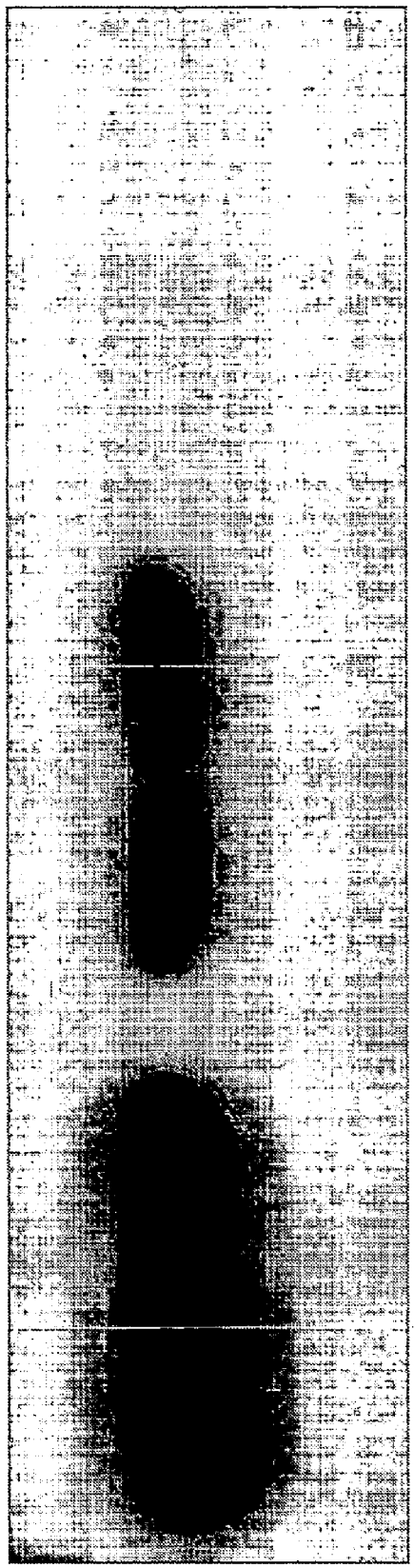
FIG. 13 shows the results of the Western blot analyzes of mouse wild homozygotes (+/+), heterozygotes (+/−) and mutant homozygotes (−/−) illustrating the expression of the Sigma-1 receptor gene in the mouse brain using a specific polyclonal antibody for the mouse Sigma-1 receptor.

Thirdly, the expression of the Sigma-1 receptor gene in the brain of mutant, heterozygous and wild mice was evaluated by locating the corresponding protein in protein extracts by way of a specific polyclonal antibody. The Western blot technique was employed for this. The results obtained are shown in FIG. 13, where no detectable protein levels were found (Sigma-1 receptor) in the brain protein extracts from mutant mice homozygous for the Sigma-1 gene.

Figure 14A:
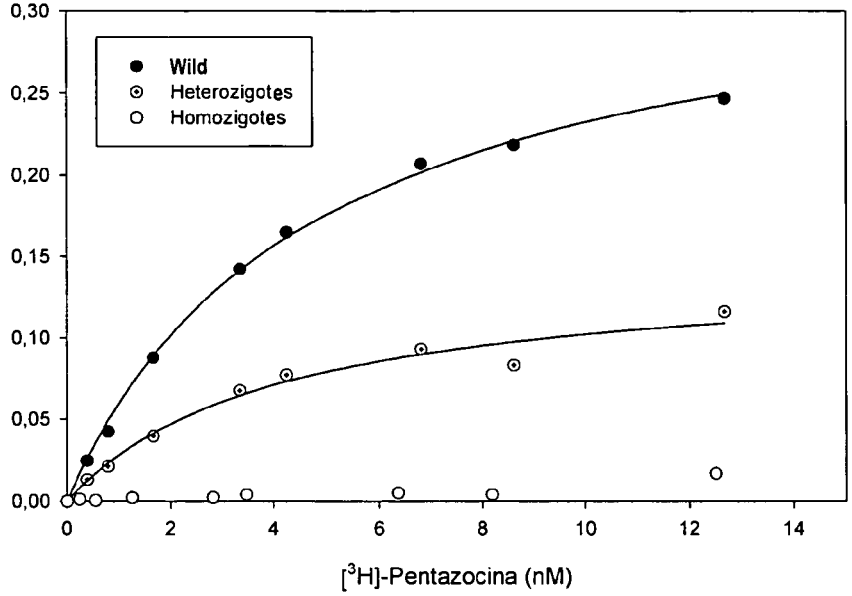
FIGS. 14A, B illustrates the activity (function) of the mouse Sigma-1 receptor by a specific binding test to the [$^3$H]-pentazocine ligand.
Figure 14B:
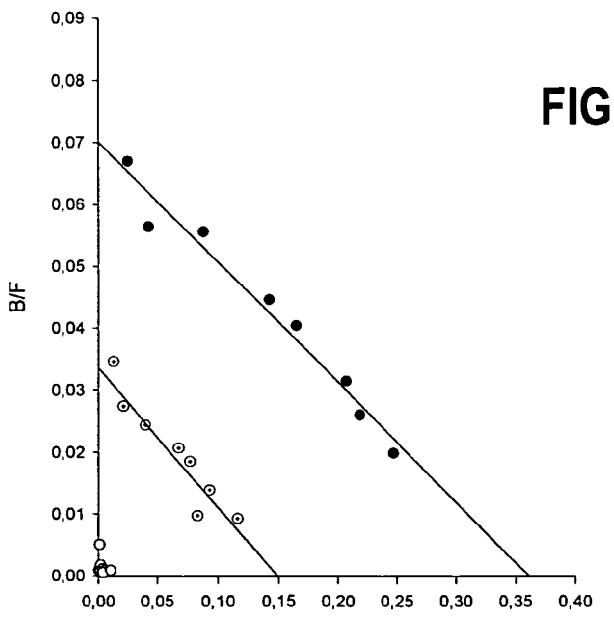
FIG. 14B is a graph representing the "bound ligand/free ligand" (B/F) ratio (ordinates) versus the bound ligand concentration (abscissas) as a function of the origin of said Sigma-1 receptors (wild homozygous, heterozygous and mutant homozygous mice).

Fourthly, the activity (function) of the mouse Sigma-1 receptor was evaluated by a specific binding test to the [$^3$H]-pentazocine ligand. Briefly, the brains of mutant (−/−), heterozygous (+/−) and wild (+/+) mice were homogenised and the homogenisations ere centrifuged several times at different speeds to obtain the membrane fraction. Then samples of the membrane fraction obtained were incubated with the [$^3$H]-pentazocine radioligand in optimal binding conditions for this receptor (37° C., for 130-170 minutes), filtrating the samples, washing them and reading the radioactivity count present in the filtrate (see DeHaven-Hudkins D. L., Fleissner L. C., Ford-Rice, F. Y. (1992) Characterization of the binding of [3H]-Pentazocine to sigma recognition sites in guinea pigs brain. European Journal of Pharmacology 227:371-378, hereinafter DeHaven-Hudkins). The results obtained are shown in FIG. 14 and reveal the lack of activity (function) in the homozygous mutant mice.

Fifthly, the function of the Sigma-1 receptor was evaluated according to known behavioral paradigms and protocols. In this sense, no statistically significant differences have been found between the behavior of the mutant and the wild mice in the following list of tests or paradigms analyzed. Statistically significant differences have only been observed with wild mice in the hyperactivity (hypermotility) response induced by the SKF-10047 ligand (data not shown).

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art. The particular implementations shown and described herein are illustrative examples of the invention and are not intended to otherwise limit the scope of the invention in any way. For the sake of brevity, conventional mechanisms and techniques may not be describes in detail, Furthermore, the connecting lines, or connectors shown in the various figures presented are intended to represent exemplary functional relationships and/or physical or logical couplings between the various elements. It should be noted that many alternative or additional functional relationships, physical connections or logical connections may be present. Moreover, no item or component is essential to the practive of the invention unless the element is specifically described as "essential" or "critical". Numerous modifications and adaptations will be readily apparent to those skilled in this art without departing from the spirit and scope of the present invention.

Biological Material Deposit

An *Escherichia coli* Top 10F' culture, known as pHR53TK, containing the pHR53TK plasmidic vector has been deposited in the Spanish Collection of Standad Cultures (Colección Española de Cultivos Tipo), CECT, Burjasot, Valencia (Spain), on 4 Oct. 2002, under the access number CECT 5737.

The invention claimed is:

1. A transgenic mutant mouse whose genome comprises a mutation that disrupts the endogenous Sigma-1 receptor gene, and the transgenic mutant mouse when homozygous for said mutation lacks detectable levels of endogenous Sigma-1 receptor and has a phenotype characterized by a statistical difference in hyperactivity response compared to wild-type control mice.

2. An isolated cell from a transgenic mouse, deficient in an endogenous Sigma-1 receptor, according to claim 1.

3. The cell according to claim 2 wherein the cell is immortalized.

4. The transgenic mutant mouse according to claim 1, wherein the genome of the transgenic mutant mouse comprises a transgene within the disrupted region introduced in the endogenous Sigma-1 receptor gene, the transgene comprises a sequence encoding a positive selection marker.

5. A transgenic mutant mouse as claimed in claim 1, wherein said transgenic mutant mouse is obtainable by the use of the vector identified as pHR53TK that is deposited in the CECT under access number CECT 5737, to insert a functional disruption in the endogenous Sigma-1 receptor gene.

6. A transgenic mutant mouse wherein said transgenic mutant mouse is an offspring of a transgenic mutant mouse according to claim 1 and is homozygous for the mutation in the endogenous Sigma-1 receptor.

7. A transgenic mutant mouse as claimed in claim 1, wherein the genome of the transgenic mutant mouse comprises a transgene within the mutation introduced in the endogenous Sigma-1 receptor gene, the transgene comprises a gene encoding a positive or negative selection marker.

8. A transgenic mutant mouse as claimed in claim 7, wherein said transgene comprises a neomycin phototransferase (neo) gene.

* * * * *